United States Patent
Imai et al.

(10) Patent No.: US 9,642,751 B2
(45) Date of Patent: May 9, 2017

(54) METHOD FOR MANUFACTURING FUSED SHEETS

(71) Applicant: KAO CORPORATION, Tokyo (JP)

(72) Inventors: Koji Imai, Ichikai-machi (JP); Shinji Hamamoto, Shimotsuke (JP); Makoto Kokubo, Yaita (JP); Takuo Yanashima, Utsunomiya (JP); Akio Morita, Ichikai-machi (JP)

(73) Assignee: KAO CORPORATION, Tokyo (JP)

( * ) Notice: Subject to any disclaimer, the term of this patent is extended or adjusted under 35 U.S.C. 154(b) by 155 days.

(21) Appl. No.: 14/390,966

(22) PCT Filed: May 14, 2013

(86) PCT No.: PCT/JP2013/063418
§ 371 (c)(1),
(2) Date: Oct. 6, 2014

(87) PCT Pub. No.: WO2013/172343
PCT Pub. Date: Nov. 21, 2013

(65) Prior Publication Data
US 2015/0064387 A1    Mar. 5, 2015

(30) Foreign Application Priority Data

May 16, 2012 (JP) ................. 2012-112263
Mar. 4, 2013 (JP) ................. 2013-042228
May 8, 2013 (JP) ................. 2013-098113

(51) Int. Cl.
*A61F 13/15*    (2006.01)
*B29C 65/16*    (2006.01)
(Continued)

(52) U.S. Cl.
CPC .. *A61F 13/15585* (2013.01); *A61F 13/15739* (2013.01); *A61F 13/565* (2013.01);
(Continued)

(58) Field of Classification Search
CPC .................................................. A61F 13/15585
(Continued)

(56) References Cited

U.S. PATENT DOCUMENTS 4,115,683 A    9/1978    Clark et al.
6,234,229 B1   5/2001    Tabuchi
(Continued)

FOREIGN PATENT DOCUMENTS

CN    1243691 A    2/2000
CN    1956836 A    5/2007
(Continued)

OTHER PUBLICATIONS

International Preliminary Report on Patentability and English translation of the Written Opinion of the International Searching Authority (Forms PCT/IB/338, PCT/IB/373 and PCT/ISA/237), dated Nov. 27, 2014, for International Application No. PCT/JP2013/063418.
(Continued)

*Primary Examiner* — Brent O'Hern
(74) *Attorney, Agent, or Firm* — Birch, Stewart, Kolasch & Birch, LLP

(57) ABSTRACT

In the present invention, one surface of a belt-shaped sheet laminate (10), in which a plurality of sheets are laminated, is pressed against a support member (21) having a light passage section (27) through which a laser beam (30) can pass, and the belt-shaped sheet laminate (10) is irradiated, from the support member (21) side via the light passage section (27), with a laser beam (30) to cut and fusion-bond the belt-shaped sheet laminate (10), thereby sealed edge sections (4) are formed by fusion-bonding the edge sections of the plurality of sheets.

4 Claims, 12 Drawing Sheets

(51) Int. Cl.
| | |
|---|---|
| B23K 26/08 | (2014.01) |
| B23K 26/38 | (2014.01) |
| B29C 65/00 | (2006.01) |
| B29C 65/74 | (2006.01) |
| A61F 13/56 | (2006.01) |
| B32B 7/04 | (2006.01) |
| B32B 37/00 | (2006.01) |
| B32B 38/00 | (2006.01) |
| B23K 26/082 | (2014.01) |
| B23K 26/40 | (2014.01) |
| B23K 26/402 | (2014.01) |
| B29L 31/48 | (2006.01) |
| B23K 103/16 | (2006.01) |
| B23K 103/00 | (2006.01) |

(52) U.S. Cl.
CPC ......... *B23K 26/082* (2015.10); *B23K 26/083* (2013.01); *B23K 26/0838* (2013.01); *B23K 26/38* (2013.01); *B23K 26/40* (2013.01); *B23K 26/402* (2013.01); *B29C 65/1648* (2013.01); *B29C 65/1658* (2013.01); *B29C 65/1696* (2013.01); *B29C 65/7473* (2013.01); *B29C 66/1122* (2013.01); *B29C 66/431* (2013.01); *B29C 66/723* (2013.01); *B29C 66/72941* (2013.01); *B29C 66/7392* (2013.01); *B29C 66/8221* (2013.01); *B29C 66/8222* (2013.01); *B29C 66/82263* (2013.01); *B29C 66/8324* (2013.01); *B29C 66/83433* (2013.01); *B29C 66/83435* (2013.01); *B32B 7/045* (2013.01); *B32B 37/0046* (2013.01); *B32B 37/0076* (2013.01); *B32B 38/0004* (2013.01); *A61F 2013/15861* (2013.01); *A61F 2013/15878* (2013.01); *A61F 2013/15918* (2013.01); *B23K 2203/172* (2015.10); *B23K 2203/42* (2015.10); *B29C 65/1619* (2013.01); *B29C 66/137* (2013.01); *B29C 66/71* (2013.01); *B29C 66/73921* (2013.01); *B29L 2031/4878* (2013.01); *B32B 2250/02* (2013.01); *B32B 2310/0843* (2013.01); *B32B 2555/02* (2013.01); *Y10T 156/1054* (2015.01); *Y10T 156/1313* (2015.01); *Y10T 428/19* (2015.01)

(58) Field of Classification Search
USPC ....................................................... 156/251
See application file for complete search history.

(56) References Cited

U.S. PATENT DOCUMENTS

| | | |
|---|---|---|
| 6,387,083 B1 | 5/2002 | Suzuki |
| 6,394,991 B1 | 5/2002 | Takei et al. |
| 2003/0213552 A1 | 11/2003 | Chen et al. |
| 2005/0224472 A1 | 10/2005 | Rasmussen et al. |
| 2006/0283846 A1 | 12/2006 | Lupinetti et al. |
| 2007/0032766 A1 | 2/2007 | Liu et al. |
| 2007/0084553 A1 | 4/2007 | Nakajima et al. |
| 2008/0145682 A1 | 6/2008 | Rasmussen et al. |
| 2008/0176023 A1 | 7/2008 | Bager et al. |
| 2010/0222756 A1* | 9/2010 | Fujioka ............... A61F 13/4942 604/365 |
| 2012/0021186 A1 | 1/2012 | Schneider |
| 2012/0095429 A1 | 4/2012 | Kobayashi et al. |
| 2013/0139960 A1 | 6/2013 | Maruyama et al. |
| 2013/0174965 A1 | 7/2013 | Yamamoto et al. |
| 2015/0064387 A1 | 3/2015 | Imai et al. |

FOREIGN PATENT DOCUMENTS

| | | |
|---|---|---|
| CN | 101068519 A | 11/2007 |
| CN | 101237840 A | 8/2008 |
| CN | 101352921 A | 1/2009 |
| CN | 101746057 A | 6/2010 |
| JP | 63-64732 A | 3/1988 |
| JP | 63-118237 A | 5/1988 |
| JP | 9-192863 A | 2/1989 |
| JP | 7-75653 A | 3/1995 |
| JP | 8-38546 A | 2/1996 |
| JP | 9-192863 A | 7/1997 |
| JP | 2000-14697 A | 1/2000 |
| JP | 2001-120595 A | 5/2001 |
| JP | 2001-145659 A | 5/2001 |
| JP | 2004-1507 A | 1/2004 |
| JP | 2004-267335 A | 9/2004 |
| JP | 2005-237768 A | 9/2005 |
| JP | 2008-546540 A | 12/2008 |
| JP | 2009-202502 A | 9/2009 |
| JP | 2009-297300 A | 12/2009 |
| JP | 2010-115849 A | 5/2010 |
| JP | 2010-125654 A | 6/2010 |
| JP | 2010-188629 A | 9/2010 |
| JP | 2011-25006 A | 2/2011 |
| JP | 2011-126011 A | 6/2011 |
| JP | 2011-131556 A | 7/2011 |
| JP | 2012-76343 A | 4/2012 |
| JP | 2012-111076 A | 6/2012 |
| JP | 2013-71282 A | 4/2013 |
| JP | 2013-529149 A | 7/2013 |
| JP | 2013-202182 A | 10/2013 |
| JP | 2013-256109 A | 12/2013 |
| JP | 2013-256133 A | 12/2013 |
| JP | 2014-124398 A | 7/2014 |
| JP | 2014-168904 A | 9/2014 |
| JP | 2015-8944 A | 1/2015 |
| JP | 2015-85091 A | 5/2015 |
| TW | 201201776 A1 | 1/2012 |
| WO | WO 2012/070462 A1 | 5/2012 |
| WO | WO 2013/172343 A1 | 11/2013 |
| WO | WO 2014/103818 A1 | 7/2014 |

OTHER PUBLICATIONS

Extended European Search Report dated Nov. 2, 2015 for Application No. 13790158.3.
International Search Report (form PCT/ISA/210), issued Sep. 22, 2014, for International Application No. PCT/JP2014/066923.
International Search Report issued in PCT/JP2013/063418, mailed on Jun. 11, 2013.
International Preliminary Report on Patentability and English translation of the Written Opinion of the International Searching Authority (forms PCT/IB/373, PCT/ISA/237 and PCT/IB/338), issued Jan. 7, 2016, for International Application No. PCT/JP2014/066923.
International Search Report (form PCT/ISA/210), dated Jan. 20, 2015, for International Application No. PCT/JP2014/078296.

\* cited by examiner

A

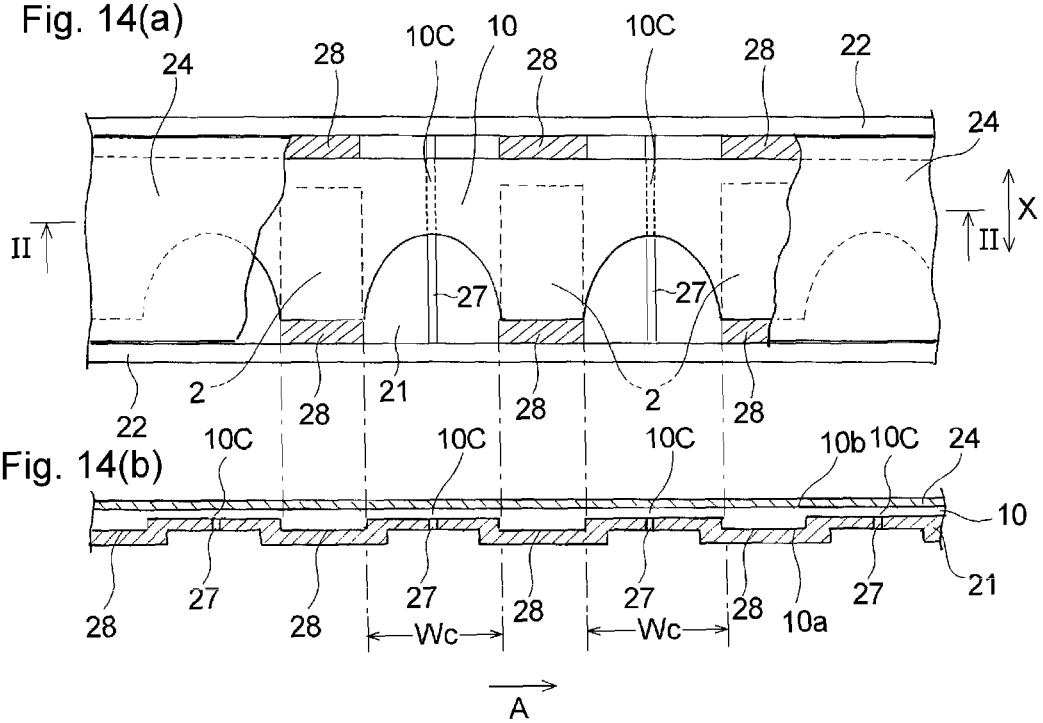

METHOD FOR MANUFACTURING FUSED SHEETS

TECHNICAL FIELD

The present invention relates to a method for manufacturing a fusion-bonded sheet article that includes sealed edge sections made by fusion-bonding edge sections of a plurality of sheets in a state where the sheets' edge sections are superposed.

BACKGROUND ART

In conventional processes for manufacturing absorbent articles such as disposable diapers or sanitary napkins, heat-roll devices are generally used for joining superposed sheets. Another known joining method is to perform joining by using a laser beam. Patent Literature 1, for example, describes a method involving: transporting a sheet laminate in which a plurality of sheets are laminated while deforming the sheet laminate into a shape conforming to the peripheral surface of a rotary roller having a laser-beam transmissive section in the peripheral surface; and, in the meantime, irradiating the sheet laminate with a laser beam from the inside of the rotary roller, and thus fusion-bonding the sheets in the sheet laminate.

Further, Patent Literature 2 describes the manufacturing of a wrapping bag having sealed edge sections made by fusion-bonding a front-side member and a back-side member, wherein a long film laminate in which a front-side member film and a back-side member film are laminated is irradiated with a laser beam and is cut and separated (molten and cut) into a plurality of pieces, and, simultaneously, the two films at the molten/cut section are fusion-bonded, to thus form the sealed edge sections. It should be noted that Patent Literature 2 is silent on how to fix the film laminate upon irradiating the film laminate with the laser beam; what Patent Literature 2 suggests is a technique of irradiating, with a laser beam, a film laminate which is in a non-fixed, free state, and cutting and separating (melting and cutting) the film laminate.

Further, Patent Literature 3 describes a technique of: superposing a plurality of metal mesh plates; and, in a state where the metal mesh plates are held in tight contact by using a clamping tool, irradiating a non-clamped section (cutting path) in the metal mesh plates with a laser beam, and thus cutting all of the sheets together to form a metal mesh cloth, and simultaneously, welding together the cut surface created in the metal mesh cloth by the laser beam.

CITATION LIST

Patent Literature

Patent Literature 1: JP 2010-188629 A
Patent Literature 2: JP 63-64732 A
Patent Literature 3: JP 64-48690 A

SUMMARY OF INVENTION

Technical Problem

A fusion-bonded sheet article made by fusion-bonding a plurality of sheets in a state where they are superposed is required to have a sufficient fusion-bond strength for practical use, such that the plurality of sheets, which are fusion-bonded together at fusion-bonded sections, do not fall apart during normal use. However, the fusion-bonded sheet articles obtained by employing the techniques described in Patent Literature 2 and 3—wherein melting/cutting and welding are executed simultaneously—have an insufficient fusion-bond strength between the sheets at fusion-bonded sections formed by laser beam irradiation (i.e., at sealed edge sections made by fusion-bonding edge sections of the sheets in a state where the sheets' edge sections are superposed). Thus, there is a possibility that the fusion-bonded sections may break and the plurality of sheets may fall apart during normal use. Further, in cases where the fusion-bonded sheet article is used, for example, for manufacturing products (sanitary products), such as absorbent articles, that are used in contact with the skin, the fusion-bonded sections need to be soft and have a pleasant texture. Patent Literature 2 and Patent Literature 3, however, fail to describe such demands/characteristics, or specific means to meet those demands.

Solution to Problem

The present invention (first invention) provides a method for manufacturing a fusion-bonded sheet article that includes sealed edge sections made by fusion-bonding edge sections of a plurality of sheets in a state where the sheets' edge sections are superposed, wherein: at least one sheet of the plurality of sheets includes a resin material; and the manufacturing method involves a step of forming the sealed edge sections by making one surface of a belt-shaped sheet laminate in which the plurality of sheets are laminated abut against a support member that has a light passage section through which a laser beam can pass, and irradiating, from the support member side via the light passage section, the belt-shaped sheet laminate which is in a pressurized state with a laser beam having a wavelength that is absorbed by the sheets constituting the sheet laminate and that causes the sheets to generate heat, and thus cutting and separating the belt-shaped sheet laminate and, simultaneously, fusion-bonding cut edge sections created, by the cutting/separation, in the plurality of sheets which are in the pressurized state.

The present invention (first invention) also provides a fusion-bonded sheet article manufactured by the aforementioned manufacturing method, wherein: in a cross-sectional view along a direction orthogonal to the direction in which the sealed edge sections extend, an outer edge of each of the sealed edge sections created by the cutting/separation has an arc shape that protrudes toward the inside of the fusion-bonded sheet article; a fusion-bonded section where the sheets constituting the fusion-bonded sheet article are fusion-bonded is formed in such a manner that the fusion-bonded section includes the outer edge of the sealed edge section and is located inwardly of the fusion-bonded sheet article from the outer edge; and, in the thickness direction of the fusion-bonded sheet article, the width of the fusion-bonded section is wider in a central section thereof than both end sections thereof.

The present invention (first invention) also provides a method for manufacturing an absorbent article, the method involving a step of manufacturing a fusion-bonded sheet article by the aforementioned manufacturing method.

The present invention (second invention) also provides a fusion-bonded sheet article manufacturing method, wherein, in the first invention: a plurality of the fusion-bonded sheet articles are manufactured continuously; and the step of forming the sealed edge sections includes: an anterior holding step of arranging the sheet laminate on the outer surface of the support member that travels in a predetermined direction, and holding the sheet laminate in a pressurized state on the outer surface of the support member; an irradiation step of irradiating the sheet laminate, which is held in the pressurized state on the outer surface of the support member, with the laser beam from an inner surface side of the support member via the light passage section, and thus cutting and separating the sheet laminate; and a posterior holding step of, after termination of the laser beam irradiation, holding the cut/separated sheet laminate on the outer surface of the support member while maintaining the pressurized state.

The present invention (second invention) also provides a fusion-bonded sheet article manufacturing device that continuously manufactures a plurality of fusion-bonded sheet articles each having sealed edge sections, by irradiating, with a laser beam, a belt-shaped sheet laminate in which a plurality of sheets are laminated and cutting and separating the sheet laminate, and fusion-bonding cut edge sections created, by the cutting/separation, in the plurality of sheets, the manufacturing device including: a support member that travels in a predetermined direction in a state where the sheet laminate is arranged on an outer surface of the support member, and that has a light passage section through which a laser beam can pass; an irradiation head that is arranged on an inner surface side of the support member and that emits the laser beam toward the support member; and a pressurizing means that pressurizes, from a side opposite from the support member, the sheet laminate which is arranged on the outer surface of the support member; wherein the support member includes an anterior holding region employed for holding the sheet laminate before being irradiated with the laser beam, a holding region employed for holding the sheet laminate during the laser beam irradiation, and a posterior holding region employed for holding the sheet laminate after being irradiated with the laser beam.

Advantageous Effects of Invention

The fusion-bonded sheet article manufacturing method of the present invention provides a fusion-bonded sheet article that has a sufficient fusion-bond strength for practical use and in which its sealed edge sections are soft and have a pleasant texture. Further, the absorbent article manufacturing method of the present invention provides an absorbent article that includes a fusion-bonded sheet article having the aforementioned advantages, and that is gentle to the wearer's skin. Further, according to the fusion-bonded sheet article manufacturing device of the present invention, such useful fusion-bonded sheet articles can be manufactured efficiently with a relatively compact device configuration.

BRIEF DESCRIPTION OF DRAWINGS

FIG. 14 shows diagrams schematically illustrating a state in which a continuous diaper strip (belt-shaped sheet laminate) is introduced to the laser joining device illustrated in FIG. 13, wherein FIG. 14(*a*) is a top view in which a pressing member (pressurizing belt) is partially cut away, and FIG. 14(*b*) is a cross-sectional view taken along line II-II of FIG. 14(*a*).

FIG. 15 is a schematic front view of the manufacturing method illustrated in FIG. 13.

DESCRIPTION OF EMBODIMENTS

The present invention relates to a method for manufacturing a fusion-bonded sheet article that includes sealed edge sections made by fusion-bonding edge sections of a plurality of sheets in a state where the sheets' edge sections are superposed, and that has a sufficient fusion-bond strength for practical use, and in which its sealed edge sections are soft and have a pleasant texture.

Figure 1:
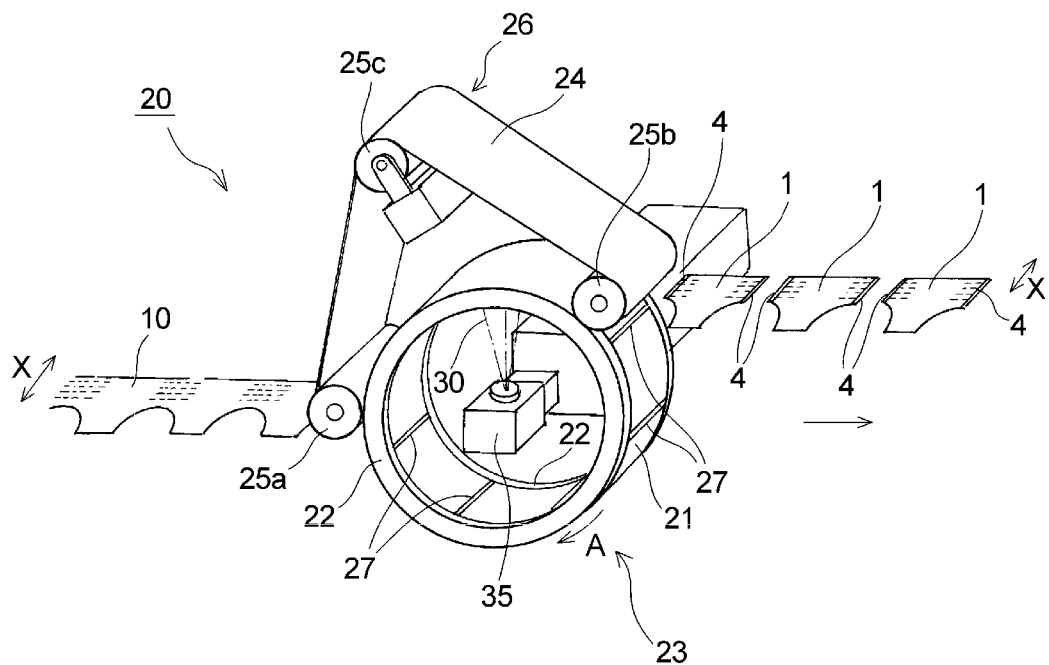
FIG. 1 is a schematic perspective view of an example of a method for manufacturing pull-on disposable diapers by using a laser joining device, which is an embodiment of an absorbent article manufacturing method of the present invention (first invention).
Figure 2:
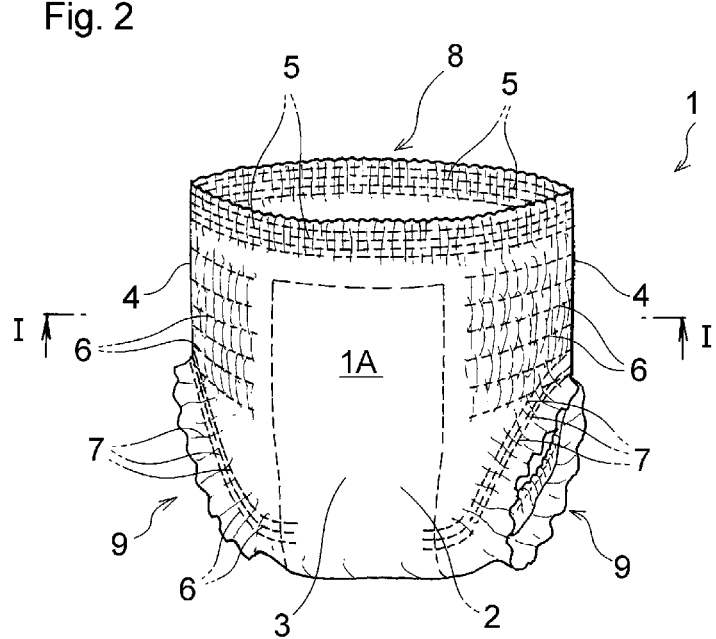
FIG. 2 is a perspective view schematically illustrating a pull-on disposable diaper manufactured by executing the manufacturing method illustrated in FIG. 1
Figure 3:
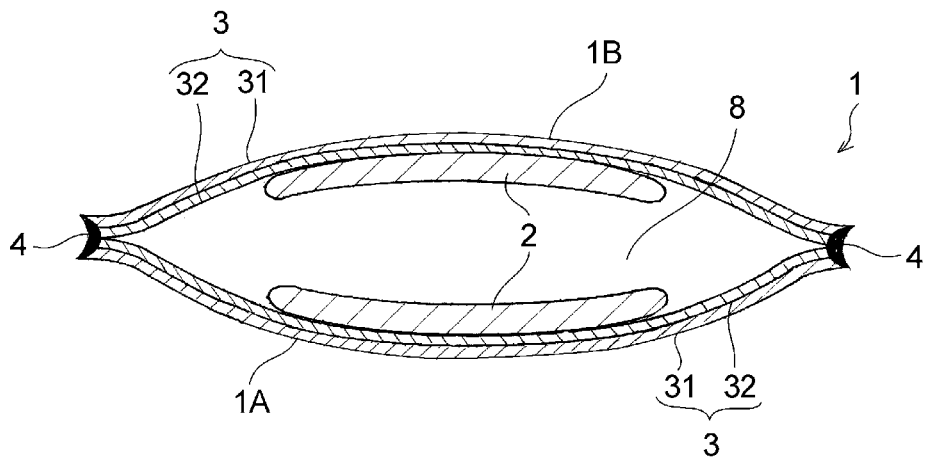
FIG. 3 is a cross-sectional view schematically illustrating the cross section taken along line I-I of FIG. 2.

A fusion-bonded sheet article manufacturing method of the present invention (first invention) will be described below—together with an absorbent article manufacturing method of the present invention which involves a step of manufacturing fusion-bonded sheet articles by the present manufacturing method—in accordance with preferred embodiments with reference to the drawings. FIG. 1 schematically illustrates a method for manufacturing pull-on disposable diapers by using a laser joining device, which is an embodiment of an absorbent article manufacturing method of the present invention. The absorbent article manufacturing method of the present invention involves a step of manufacturing a "fusion-bonded sheet article that includes sealed edge sections made by fusion-bonding edge sections of a plurality of sheets in a state where the sheets' edge sections are superposed"; in the diaper manufacturing method of the present embodiment as illustrated in FIG. 1, a pull-on disposable diaper 1 that includes an outer cover 3 having a pair of side seal sections 4, 4, as illustrated in FIGS. 2 and 3, is manufactured as the fusion-bonded sheet article. Note that the outer cover 3 and the diaper 1 including the outer cover are both fusion-bonded sheet articles.

As illustrated in FIGS. 2 and 3, the diaper 1 is a pull-on disposable diaper including an absorbent assembly 2, and an outer cover 3 that is arranged on a skin-non-contacting surface side of the absorbent assembly 2 and to which the absorbent assembly 2 is fixed, wherein a pair of side seal sections 4, 4, a waist opening 8, and a pair of leg openings 9, 9 are formed by joining both side edge sections of the outer cover 3 in a stomach-side section 1A and both side edge sections of the outer cover 3 in a back-side section 1B. The side seal sections 4 correspond to the aforementioned "sealed edge sections made by fusion-bonding edge sections of a plurality of sheets in a state where the sheets' edge sections are superposed".

In the diaper manufacturing method of the present embodiment, a continuous diaper strip 10 (continuous absorbent-article strip) in which sheet laminates including a plurality of sheets (precursors of pull-on disposable diapers in which side seal sections have not yet been formed) are arranged continuously in one direction is manufactured separately as a "belt-shaped sheet laminate in which a plurality of sheets are laminated", and then, pull-on disposable diapers 1 (fusion-bonded sheet articles) each including an outer cover 3 (fusion-bonded sheet article) having a pair of side seal sections 4, 4 (sealed edge sections) are manufactured continuously by irradiating the continuous diaper strip 10 with a laser beam 30 as illustrated in FIG. 1, and thus, cutting and separating the continuous diaper strip into separate pieces, and, simultaneously, fusion-bonding the cut edge sections created, by the cutting/separation, in the plurality of sheets which are in a pressurized state.

In the aforementioned "belt-shaped sheet laminate in which a plurality of sheets are laminated", it is preferable that at least one sheet of the plurality of sheets includes a resin material and is formed by employing the resin material as a main component. More specifically, for example, it is preferable that at least one sheet of the sheets includes a heat-fusible synthetic resin—such as polyethylene, polyethylene terephthalate, or polypropylene—as the resin material, and is, for example, a nonwoven fabric, a film, or a laminate sheet made of a nonwoven fabric and a film. Examples of nonwoven fabrics include air-through nonwoven fabrics, heat-rolled nonwoven fabrics, spun-laced nonwoven fabrics, spun-bonded nonwoven fabrics, and melt-blown nonwoven fabrics. It is preferable that, in the sheet laminate, all of the plurality of sheets constituting the sheet laminate include a resin material. First, a method for manufacturing a continuous diaper strip 10 (belt-shaped sheet laminate) will be described below with reference to FIG. 4.

Figure 4:
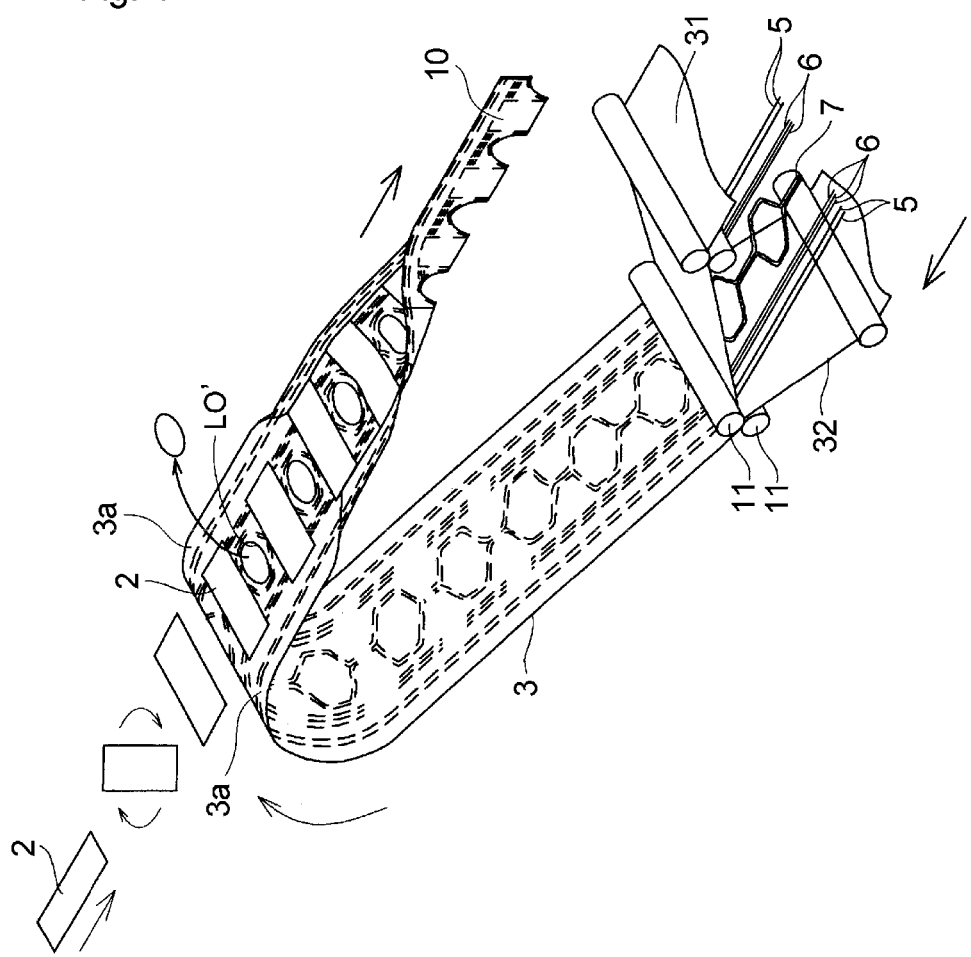
FIG. 4 is a perspective view schematically illustrating steps for manufacturing a continuous diaper strip (belt-shaped sheet laminate) illustrated in FIG. 1.

First, as illustrated in FIG. 4, a plurality of waist section elastic members 5 that form waist gathers, a plurality of hip section elastic members 6 that form hip gathers, and a plurality of leg section elastic members 7 that form leg gathers are arranged in their stretched state, wherein they have been extended to a predetermined extension ratio, between a belt-shaped outer layer sheet 31 that is continuously supplied from an original textile roll (not illustrated) and a belt-shaped inner layer sheet 32 that is continuously supplied from an original textile roll (not illustrated). Here, in the present embodiment, a hot-melt adhesive is continuously or intermittently applied to the waist section elastic members 5 and the hip section elastic members 6 with an adhesive applicator (not illustrated), and the leg section elastic members 7 are arranged so as to form a predetermined leg-surrounding pattern by means of a known oscillating guide (not illustrated) that reciprocates orthogonally to the flow direction of the sheets. Further, before superposing the belt-shaped outer layer sheet 31 and the belt-shaped inner layer sheet 32, a hot-melt adhesive is applied with an adhesive applicator (not illustrated) to predetermined sections on the opposing surface(s) of one or both of the sheets. It should be noted that, in cases where the elastic members, such as the waist section elastic members 5 and the hip section elastic members 6, are arranged in their stretched state so as to cross over a section in the sheets 31, 32 that is to be cut and separated by laser beam irradiation (i.e., "a section where a side seal section 4 is to be formed") (a "section-to-be-cut/separated" as illustrated by reference sign 10C in FIG. 5), it is preferable to apply an adhesive to that section and the vicinity thereof in order to avoid disadvantages such as the falling-off or significant shrinking of the elastic members after the cutting/separation.

Then, as illustrated in FIG. 4, by feeding the belt-shaped outer layer sheet 31 and the belt-shaped inner layer sheet 32—with the waist section elastic members 5, hip section elastic members 6, and leg section elastic members 7 sandwiched therebetween in their stretched state—between a pair of nip rollers 11, 11 and pressurizing the sheets, a belt-shaped outer cover 3 is formed, which includes a plurality of elastic members 5, 6, 7 arranged in their stretched state between the belt-shaped sheets 31, 32. Then, in the present embodiment, by using an elastic member pre-cutting means (not illustrated), the plurality of hip section elastic members 6 and the plurality of leg section elastic members 7 are pressed at locations corresponding to the locations for arranging the later-described absorbent assemblies 2, and are cut and separated into a plurality of separate pieces so that their contracting function is not exerted. An example of the elastic member pre-cutting means includes the elastic member cutting unit used in the method for manufacturing composite elastic members as described in JP 2002-253605 A.

Next, as illustrated in FIG. 4, an adhesive such as a hot-melt adhesive is applied in advance to each of a plurality of absorbent assemblies 2 that have been manufactured in a separate step, each absorbent assembly 2 is rotated by 90 degrees, and the absorbent assemblies 2 are intermittently supplied and fixed onto the inner layer sheet 32 constituting the belt-shaped outer cover 3. It should be noted that the adhesive for fixing the absorbent assembly may be applied in advance to locations on the inner layer sheet 32 where the absorbent assemblies 2 are to be arranged, and not to the absorbent assemblies 2.

Then, as illustrated in FIG. 4, a leg hole LO' is formed within each annular section that is annularly surrounded by the leg section elastic members 7 in the belt-shaped outer cover 3 on which the absorbent assemblies 2 have been arranged. This leg hole forming step can be executed by using a method/means similar to conventional methods/means, such as a rotary cutter or a laser cutter, for manufacturing this type of article. It should be noted that, in the present embodiment, the leg holes are formed after arranging the absorbent assemblies 2 to the belt-shaped outer cover 3, but the leg holes may be formed before arranging the absorbent assemblies 2.

Next, the belt-shaped outer cover 3 is folded in its width direction (direction orthogonal to the direction in which the outer cover 3 is transported). More specifically, as illustrated in FIG. 4, both side sections 3a, 3a along the transporting direction of the belt-shaped outer cover 3 are folded back so as to cover both lengthwise end sections of each absorbent assembly 2 and are fixed onto the absorbent assembly 2's lengthwise end sections, and then, the outer cover 3 is folded in two in its width direction together with the absorbent assemblies 2. Thus, the intended continuous diaper strip 10 (belt-shaped sheet laminate) is obtained.

In the diaper manufacturing method of the present embodiment, as illustrated in FIG. 1, the continuous diaper strip 10 (belt-shaped sheet laminate), which has been thus-manufactured separately, is irradiated with a laser beam by using a laser joining device 20 ("device for manufacturing a fusion-bonded sheet article that includes sealed edge sections made by fusion-bonding edge sections of a plurality of sheets in a state where the sheets' edge sections are superposed"), and thus, pull-on disposable diapers 1 (fusion-bonded sheet articles) each including an outer cover 3 (fusion-bonded sheet article) having a pair of side seal sections 4, 4 (sealed edge sections) are manufactured continuously.

The laser joining device 20 will be described. As illustrated in FIG. 1, the laser joining device 20 includes: a hollow cylindrical roller 23 provided with a cylindrical (annular) support member 21 that is driven to rotate in the direction of arrow A; an irradiation head 35 arranged in a hollow section of the support member 21 and emitting a laser beam 30; and, as a pressurizing means, a belt-type pressurizing device 26 provided with an endless pressurizing belt 24 (pressing member) and a plurality of (three) rollers 25a, 25b, 25c that rotate in a state where the pressurizing belt 24 is looped over the rollers. The laser joining device 20 includes a tension adjustment mechanism (not illustrated) that can increase/decrease and adjust the tension on the pressurizing belt 24 to be wrapped around the outer peripheral surface of the annular support member 21 (the peripheral surface section of the cylindrical roller 23). By adjusting the tension, the pressure applied to the continuous diaper strip 10 (sheet laminate) by the support member 21 and the pressurizing belt 24 can be adjusted as appropriate.

The support member 21 forms the peripheral surface section (the section that abuts against the workpiece) of the cylindrical roller 23, and is sandwiched and fixed between a pair of annular frame bodies 22, 22 forming the respective left-and-right side edge sections of the cylindrical roller 23. In the present embodiment, the support member 21 is made of a single annular member having the same length as the circumferential length of each annular frame body 22, and is made of a metal material, such as iron, aluminum, stainless steel, or copper, or a heat-resistant material, such as a ceramic.

Figure 5A:
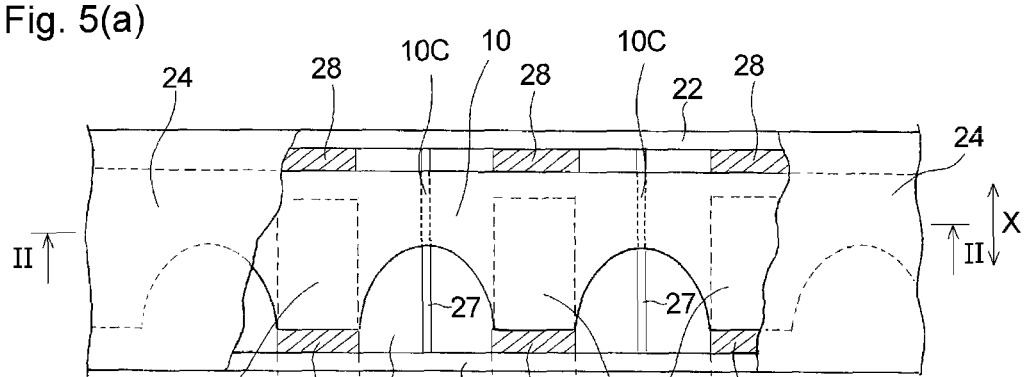
FIG. 5 shows diagrams schematically illustrating a state in which the continuous diaper strip (belt-shaped sheet laminate) is introduced to the laser joining device illustrated in FIG. 1, wherein FIG. 5(*a*) is a top view in which a pressing member is partially cut away, and FIG. 5(*b*) is a cross-sectional view taken along line II-II of FIG. 5(*a*).
Figure 5B:
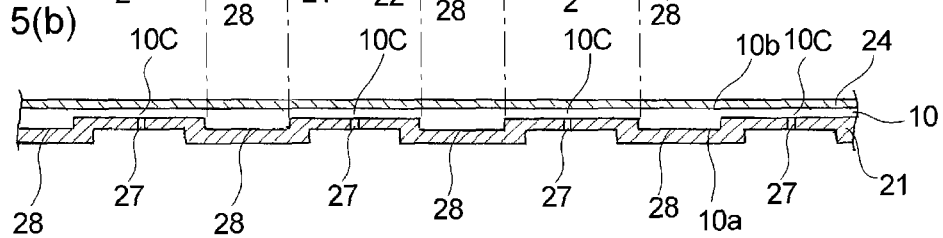

The support member 21 has light passage sections through which the laser beam can pass. As illustrated in FIGS. 1 and 5, the support member 21 of the present embodiment has, as the light passage sections, slit-shaped openings 27 that penetrate the support member 21 in the thickness direction. It should be noted that, in FIG. 5 (FIG. 5(b)), it is described as if the support member 21, the pressurizing belt 24 (pressing member), and the continuous diaper strip 10 (sheet laminate) sandwiched therebetween are moving horizontally from the left side toward the right side in FIG. 5 for the sake of brevity of explanation; in reality, however, these members move so as to rotate in a curved state corresponding to the cylindrical (annular) shape of the cylindrical roller 23. Each opening 27 is rectangular in a planar view, and its length direction matches the width direction of the support member 21 (the direction indicated by the reference sign X in FIG. 5(a); the direction parallel to the rotation axis of the cylindrical roller 23), and a plurality of the openings 27 are formed with predetermined intervals therebetween in the circumferential direction of the cylindrical support member 21. The support member 21 allows the laser beam to pass through at the openings 27, but does not allow the passage (transmission) of the laser beam at sections other than the openings 27. Methods for forming openings 27 in the support member 21 include: (1) a method of piercing the openings 27 by performing, for example, etching, punching, or laser processing, at predetermined sections in the support member 21; or (2) a method of using a plurality of curved rectangular members as the support member 21 instead of the single annular member, and arranging these members between the pair of frame bodies 22, 22 while leaving predetermined gaps therebetween in the circumferential direction of the frame bodies 22. In the method (2), the gap between two adjacent members becomes the slit-shaped opening 27.

It should be noted that, in this laser joining device 20 ("device for manufacturing a fusion-bonded sheet article that includes sealed edge sections made by fusion-bonding edge sections of a plurality of sheets in a state where the sheets' edge sections are superposed"), the (slit-shaped) opening 27 penetrating the support member 21 in the thickness direction constitutes the light passage section through which the laser beam can pass. Thus, a section of the continuous diaper strip 10 (sheet laminate) that overlaps the opening 27 (i.e., the section-to-be-cut/separated 10C) is in abutment with the pressurizing belt 24, but is not sandwiched between the support member 21 and the pressurizing belt 24 (pressing member). Thus, strictly speaking, the section-to-be-cut/separated 10C does not receive pressurizing force created by being sandwiched between the members 21, 24. Even though the section-to-be-cut/separated 10C overlapping the opening 27 is not sandwiched by the members 21, 24, the vicinity thereof—i.e., sections of the continuous diaper strip 10 that overlap the vicinity (opening edge section) of the opening 27—is sandwiched by the members 21, 24. Thus, the section-to-be-cut/separated 10C does not move before and after laser beam irradiation, and thus, the cut edge sections that have been created by cutting/separating the continuous diaper strip 10 by laser beam irradiation do not move. In other words, the section-to-be-cut/separated 10C in the continuous diaper strip 10 (section of the sheet laminate overlapping the opening 27) is a section restricted by the pressurizing force created by being sandwiched between the members 21, 24, and is a section that is virtually affected by the pressurizing force.

As illustrated in FIG. 5(b), the support member 21 has recesses 28 in its outer surface (the surface abutting against the workpiece). A plurality of the recesses 28 are formed at predetermined intervals in the circumferential direction of the cylindrical support member 21, and each slit-shaped opening 27 is formed in a region (i.e., protruding section) located between two adjacent recesses 28, 28. Each opening 27 is formed in the center of the protruding section in the circumferential direction of the cylindrical support member 21.

By forming the recesses 28 in the outer surface of the support member 21, it is possible to introduce the continuous diaper strip 10 on the outer surface of the support member 21 in such a manner that, if the thickness of the continuous diaper strip 10 (belt-shaped sheet laminate) is not uniform, the relatively thick parts in the continuous diaper strip 10 (e.g., the regions where the absorbent assemblies 2 are arranged) are accommodated in the recesses 28. By introducing the continuous diaper strip 10 onto the support member 21 in this way, the surface (the "other surface 10b") of the continuous diaper strip 10 abutting against the pressurizing belt 24 (pressing member) becomes substantially flat as illustrated in FIG. 5(b), and thus, when the pressurizing belt 24 is pressed against the continuous diaper strip 10, the entire section, in the continuous diaper strip 10, located on each protruding section where each opening 27 is formed (i.e., the section-to-be-cut/separated 10C and the vicinity thereof as illustrated in FIG. 5) is pressurized uniformly in the thickness direction by the pressurizing belt 24 and by the wrapping of the continuous diaper strip 10 onto the support member 21 by a predetermined tension. Thus, when this section, which is pressurized in the thickness direction before being cut/separated by laser beam irradiation, is irradiated with a laser beam and is cut and separated, the cut edge sections of the plurality of sheets constituting the cut/separated section can be fusion-bonded more reliably, and the fusion-bond strength of the side seal sections 4 (sealed edge sections) can be further improved.

The belt-type pressurizing device 26 includes: the endless pressurizing belt 24 (pressing member); and three rollers 25a, 25b, 25c that rotate in a state where the pressurizing belt 24 is looped over them. The rollers 25a, 25b, 25c may be drive rollers, or may be driven rollers that follow the rotation of the cylindrical roller 23. As one or more of the rollers 25a, 25b, 25c are driven to rotate, the pressurizing belt 24 moves at the same speed as the cylindrical roller 23 (support member 21). It is preferable that the temperature of the support member 21 and the pressurizing belt 24 is maintained within a predetermined temperature range by air cooling, water cooling, or the like.

As for the pressurizing belt 24 (pressing member), it is possible to use a metal- or resin-made belt having heat resistance that can endure the heat generated during processing. The pressurizing belt 24 of the present embodiment is made of a metal material, such as iron, aluminum, or stainless steel. Further, in general, a belt that is not transmissive to the laser beam emitted onto the workpiece (continuous diaper strip 10) is used as the pressurizing belt 24, but a belt having such transmissivity may be used instead.

As illustrated in FIG. 1, in the hollow section of the hollow cylindrical roller 23 (support member 21) is provided an irradiation head 35 that emits a laser beam 30 toward the support member 21 forming the peripheral surface section of the cylindrical roller 23. The irradiation head 35 is a galvanoscanner (device with a mirror on the motor shaft) that can make the laser beam 30 scan freely, and includes, for example: a mechanism that makes the laser beam 30 move to and fro in a direction parallel to the rotation axis of the cylindrical roller 23 (i.e., the direction indicated by the reference sign X in FIG. 5(a)); a mechanism for moving, in the circumferential direction of the cylindrical roller 23, the position (irradiation point) where the laser beam 30 is incident on the continuous diaper strip 10 on the support member 21; and a mechanism for keeping the spot diameter of the laser beam 30 constant on the peripheral surface of the cylindrical roller 23. With this configuration, the laser irradiation mechanism can move the irradiation point of the laser beam 30 discretionarily in both the circumferential direction of the cylindrical roller 23 and a direction orthogonal to the circumferential direction (i.e., the direction indicated by the reference sign X in FIG. 5(a); the direction parallel to the rotation axis of the cylindrical roller 23).

As illustrated in FIG. 1, the continuous diaper strip 10 (belt-shaped sheet laminate) is introduced onto the outer surface of the support member 21, which forms the peripheral surface section of the cylindrical roller 23 driven to rotate in the direction of arrow A, in a state where a predetermined tension is applied thereto by guide rollers, etc. (not illustrated). The continuous diaper strip 10 is then transported by a predetermined distance by the rotation of the cylindrical roller 23 in the circumferential direction thereof in a manner so as to be wrapped around the support member 21. Thereafter, the continuous diaper strip 10 is separated from the support member 21 by discharge rollers and nip rollers (not illustrated). By transporting the continuous diaper strip 10 in a manner so as to be wrapped around the support member 21, which forms the peripheral surface section of the cylindrical roller 23, with a predetermined tension applied thereto and so as to be pressurized by the pressurizing belt 24, sections of the continuous diaper strip 10 that are sandwiched between the support member 21 and the pressurizing belt 24, as well as the vicinity of those sections, are brought into a state where they are pressurized (compressed) in the thickness direction before being cut and separated by laser beam irradiation. Thus, in cases where, for example, the continuous diaper strip 10 includes a nonwoven fabric, the continuous diaper strip 10 can be compressed more efficiently, and as a result, when the continuous diaper strip 10 in its compressed state is irradiated with a laser beam and is cut and separated, the cut edge sections of the plurality of sheets that constitute the cut/separated section can be fusion-bonded more reliably, thus further increasing the fusion-bonding strength of the side seal sections 4 (sealed edge sections).

The angle of rotation of the support member 21 (cylindrical roller 23) from when the continuous diaper strip 10 is introduced onto the support member 21 until it separates therefrom may be, for example, 90 to 270 degrees, and more preferably 120 to 270 degrees. Further, the angular range (range of press-contact angle) for pressing the continuous diaper strip 10 into contact with the support member 21 by the pressurizing belt 24 (pressing member) is preferably 90 to 270 degrees and more preferably 120 to 270 degrees, if a case where the continuous diaper strip 10 is pressed in contact with the cylindrical support member 21 (cylindrical roller 23) over the entire perimeter in its circumferential direction is considered as 360 degrees.

In the diaper manufacturing method of the present embodiment, as illustrated in FIGS. 1 and 5, while the continuous diaper strip 10 (belt-shaped sheet laminate) is continuously transported, one surface 10a thereof is made to abut against the outer surface of the support member 21—which forms the peripheral surface section of the cylindrical roller 23 and which has slit-shaped openings 27 (light passage sections) through which the laser beam 30 can pass—and by irradiating the continuous diaper strip 10, which is in a pressurized state, with the laser beam 30 from the support member 21 side via the opening 27, the continuous diaper strip 10 is cut and separated and, simultaneously, the cut edge sections, which have been created by the cutting and separation, in the plurality of sheets in the aforementioned pressurized state are fusion-bonded together. Thus, side seal sections 4 (sealed edge sections) are formed.

More specifically, as illustrated in FIGS. 1 and 5, the pressurizing belt 24 (pressing member) is pressed against the other surface 10b of the continuous diaper strip 10 which is in abutment with the support member 21 (i.e., the surface on the opposite side from the one surface 10a which is the surface abutting against the support member 21), and the continuous diaper strip 10 in the aforementioned state is irradiated with a laser beam 30 from the support member 21 side via the slit-shaped opening 27, to thus continuously manufacture diapers 1 (fusion-bonded sheet articles) each including an outer cover 3 (fusion-bonded sheet article) having a pair of side seal sections 4, 4 (sealed edge sections). From the viewpoint of reliably fusion-bonding the cut edge sections created in the plurality of sheets by the irradiation and improving the fusion-bond strength of the side seal sections 4, it is preferable to irradiate the continuous diaper strip 10 with the laser beam 30 in a state where the continuous diaper strip is in a pressurized state (compressed state) by being sandwiched between the support member 21 and the pressurizing belt 24.

Figure 6A:
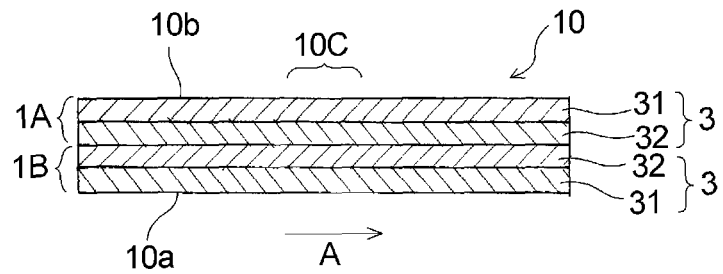
FIGS. 6(*a*) to 6(*c*) are explanatory diagrams each explaining how the continuous diaper strip (belt-shaped sheet laminate) is cut and separated and, simultaneously, side seal sections (sealed edge sections) are formed by using the laser joining device illustrated in FIG. 1.

FIG. 6 explains how the continuous diaper strip 10 (belt-shaped sheet laminate) is cut and separated simultaneously with forming side seal sections 4 (sealed edge sections) by using the laser joining device 20. FIG. 6(a) schematically illustrates a section 10C in the continuous diaper strip 10 to be cut/separated by the laser beam 30 and the vicinity thereof. As illustrated in FIG. 5(a), the section-to-be-cut/separated 10C in the continuous diaper strip 10 in the present embodiment is located in the center, in the length direction (transporting direction A), of a region in the continuous diaper strip 10 where absorbent assemblies 2 are not arranged. The section-to-be-cut/separated 10C is constituted by: an eight-layer structure section—wherein eight sheets are layered—in the end section of the waist opening 8 (cf. FIG. 2) and the vicinity thereof; and a four-layer structure section—wherein four sheets are layered—in other sections. As illustrated in FIG. 6(a), the four-layer structure section is made of two sheets (outer layer sheet 31 and inner layer sheet 32) constituting a single outer cover 3 in the stomach-side section 1A, and two sheets 31, 32 constituting a single outer cover 3 in the back-side section 1B, and is constituted by layering these four sheets. On the other hand, in the eight-layer structure section, because both side sections 3a, 3a of the belt-shaped outer cover 3 have been folded back so as to cover both lengthwise end sections of each absorbent assembly 2 at the time of manufacturing the continuous diaper strip 10 as described above (cf. FIG. 4), two outer covers 3 exist in each of the stomach-side section 1A and the back-side section 1B—which means that four outer covers 3, 3 are layered—and thus, eight sheets 31, 32 are layered. It should be noted that, in both the four-layer structure section and the eight-layer structure section, elastic members—such as the waist section elastic members 5 or hip section elastic members 6—may be interposed and arranged between mutually superposed sheets 31, 32, but for the sake of brevity of explanation, the elastic members are omitted from FIG. 6. The description below mainly concerns the four-layer structure section, but unless stated otherwise, the eight-layer structure section is structured like the four-layer structure section and has side seal sections 4 formed therein.

In the four-layer-structure section-to-be-cut/separated 10C in the continuous diaper strip 10, one of, or all of, the outer layer sheet 31 constituting one surface 10a (the surface abutting against the support member 21) of the continuous diaper strip 10 and the sheets (inner layer sheets 32) other than the sheet constituting the aforementioned one surface 10a is/are a sheet that generates heat by absorbing the laser beam 30. In the present embodiment, all four sheets 31, 32 constituting the section-to-be-cut/separated 10C are sheets (nonwoven fabrics) that generate heat by absorbing the laser beam 30. Further, prior to irradiation with the laser beam 30, the two mutually-superposed sheets in the section-to-be-cut/separated 10C and the vicinity thereof may be joined by an adhesive etc., or do not have to be joined at all.

Figure 6B:
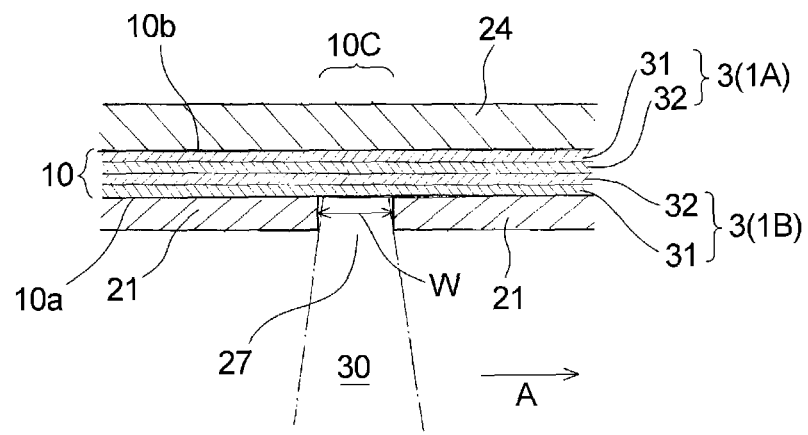

As illustrated in FIG. 6(b), the continuous diaper strip 10 is introduced onto the support member 21, which rotates in the direction of arrow A, in such a manner that the aforementioned one surface 10a abuts against the support member 21 and the section-to-be-cut/separated 10C is positioned on the slit-shaped opening 27. Also, the continuous diaper strip 10 is pressurized (compressed) in the thickness direction while being transported in the direction of arrow A due to the other surface 10b being pressed by the pressurizing belt 24 (pressing member). Then, the section-to-be-cut/separated 10C, which is being transported in this pressurized state, is irradiated with the laser beam 30 from the support member 21 side via the opening 27. As described above, the irradiation point of the laser beam 30 is configured so as to be discretionarily movable in the circumferential direction of the cylindrical roller 23, and is set so as to follow the movement of the opening 27 along the circumferential direction. Thus, while being transported, the section-to-be-cut/separated 10C positioned on the opening 27 is irradiated with the laser beam 30 continuously for a certain period of time.

Figure 6C:
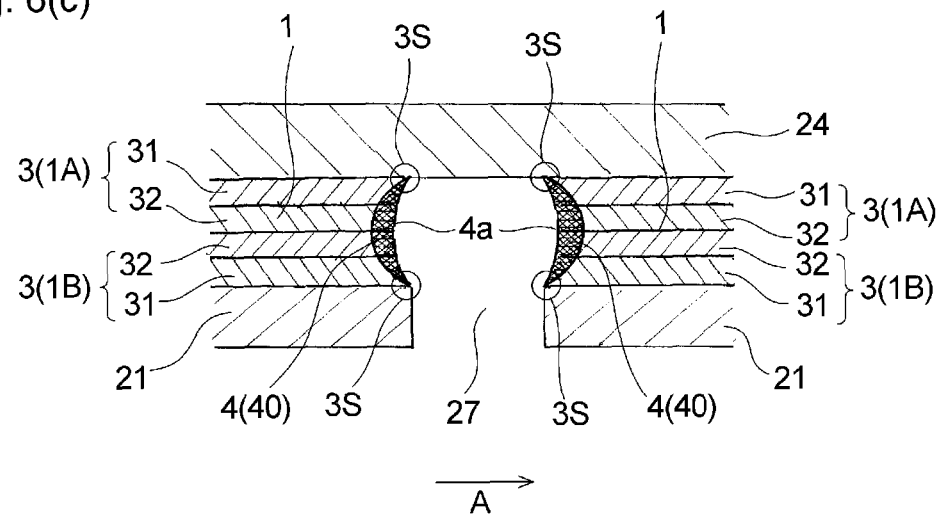

When the four-layer-structure section-to-be-cut/separated 10C is irradiated with the laser beam 30, the materials (fibers, etc.) forming the sheets 31, 32 in the section-to-be-cut/separated 10C generate heat due to direct exposure to the laser beam 30, and thus evaporate and disappear. Meanwhile, the aforementioned sheet-forming materials in the vicinity of the section-to-be-cut/separated 10C are indirectly heated by the laser beam 30 and melt. As a result, as illustrated in FIG. 6(c), the four-layer-structure section-to-be-cut/separated 10C is molten and cut, and thus, the continuous diaper strip 10 is cut and separated in such a manner that a single sheet laminate (diaper precursor) is isolated from the continuous diaper strip 10, and simultaneously, the cut edge sections created, by the cutting/separation, in the four sheets 31, 32 in the isolated sheet laminate, as well as the cut edge sections in the four sheets 31, 32 in the continuous diaper strip 10 from which the sheet laminate has been isolated, are fusion-bonded. These cut edge sections have been in a pressurized state (compressed state) by being sandwiched between the support member 21 and the pressurizing belt 24, even before their formation (i.e., before the continuous diaper strip 10 is cut and separated by being irradiated with the laser beam 30). According to the diaper manufacturing method of the present embodiment, the cutting/separation of the belt-shaped sheet laminate and the fusion-bonding of the sheets' cut edge sections, which have been created in two sites by the cutting/separation and which are in a pressurized state, are performed simultaneously by a single laser beam irradiation. Thus, compared to methods in which two fusion-bonded sites are formed by performing laser beam irradiation twice (i.e., methods outside the scope of the present invention), fusion-bonding and cutting/separation can be performed in a single step with substantially half the laser output, and thus, diapers 1 can be manufactured efficiently. Further, because fusion-bonding and cutting/separation can be performed in the same step, non-sealed edge sections—in which the sheets' cut edge sections are not fusion-bonded together—will not be created, and thus, this step is also effective in material reduction.

The cut edge sections of the sheets 31, 32 are in a molten state due to heat generation during, and immediately after the termination of, the irradiation with the laser beam 30. However, after the termination of irradiation, the cut edge sections are easily cooled by the contact with the support member 21 and are rapidly cooled and solidify due to the transmission of heat to outside air and to the support member 21 and the pressurizing belt 24, while the continuous diaper strip 10 and the single piece of sheet laminate (diaper precursor) isolated from the continuous diaper strip 10 by irradiation with the laser beam 30 are kept in their pressurized state by the support member 21 and the pressurizing belt 24. Thus, the cut edge sections are made into fusion-bonded sections 40 in which the materials (fibers, etc.) forming the cut edge sections are molten and integrated together. By the formation of the fusion-bonded section 40, one side seal section of the pair of side seal sections 4, 4 in a single diaper 1 is formed (that is, the fusion-bonded section 40 becomes the side seal section 4). It should be noted that, if necessary, the cut edge sections of the sheets 31, 32 may be forcibly cooled by a known cooling means, such as a suction device or an air exhaust device, to promote the formation of the fusion-bonded sections 40.

After a single section-to-be-cut/separated 10C is cut and separated, the laser beam 30 is moved so that its irradiation point is incident on another opening 27 adjacent to the current opening in a direction opposite to the transporting direction A, and the laser beam 30 is emitted through this other opening 27 onto another section-to-be-cut/separated 10C which is positioned thereon. Thus, this other section-to-be-cut/separated 10C is cut/separated and fusion-bonded in the same manner, and the other side seal section 4 (fusion-bonded section 40) forming a pair with the previously-formed side seal section 4 is formed. The same operation is repeated thereafter, thus continuously manufacturing pull-on disposable diapers 1 (fusion-bonded sheet articles) each including an outer cover 3 (fusion-bonded sheet article) having a pair of side seal sections 4, 4 (sealed edge sections). As described above, in the diaper manufacturing method of the present embodiment, the side seal sections (fusion-bonded sections) in each diaper 1 are formed by fusion-bonding by laser beam irradiation, and are not formed by other fusion-bonding methods.

Figure 7:
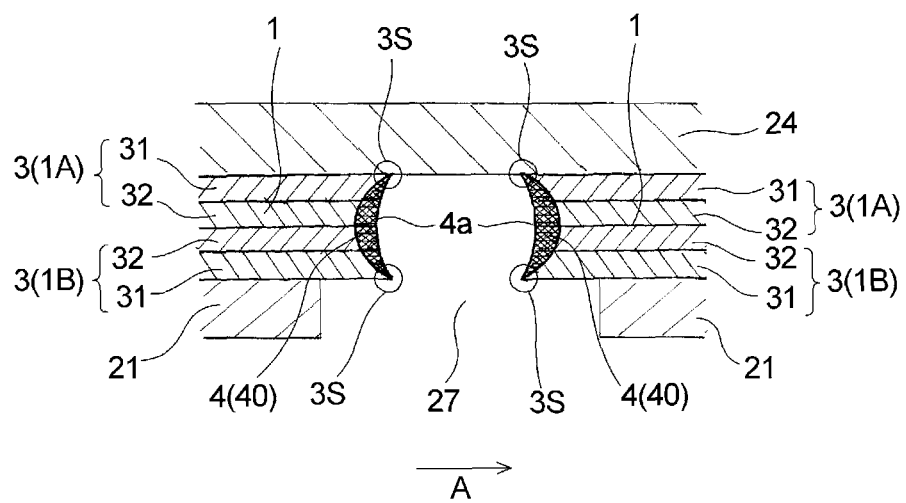
FIG. 7 is a diagram corresponding to FIG. 6(*c*), illustrating another example of a pull-on disposable diaper manufacturing method using the laser joining device illustrated in FIG. 1.

It should be noted that, if the diameter Φ of the spot of the laser beam 30 (i.e., section irradiated with the laser beam 30) on the continuous diaper strip 10 (belt-shaped sheet laminate) is smaller than the width W (cf. FIG. 6(*b*); the length of the opening 27 along the circumferential direction of the cylindrical roller 23) of the slit-shaped opening 27 through which the laser beam 30 is emitted (i.e., if Φ/W is less than 1), then, as illustrated in FIG. 7, the pair of side seal sections 4, 4 (fusion-bonded sections 40, 40) formed by the irradiation with the laser beam 30 may be located in a section, of the continuous diaper strip 10, that overlaps the opening 27 (i.e., in a section sandwiched between a pair of opening edge sections of the slit-shaped opening 27 that extend along a direction orthogonal to the transporting direction A in a planar view). In other words, the fusion-bonded sections 40 can be formed—even in a section, of the continuous diaper strip 10, that is not sandwiched between the support member 21 and the pressurizing belt 24 (pressing member)—so long as the section is in the vicinity (i.e., the opening edge section) of the opening 27, i.e., a section that is virtually affected by the pressurizing force caused by the sandwiching of the members 21, 24, as described above.

One main characteristic feature of the diaper 1 manufactured as above lies in the side seal sections 4. As illustrated in FIG. 6(*c*) or FIG. 7, in a cross-sectional view along a direction (the width direction of the diaper 1) that is orthogonal to the direction in which the side seal section 4 extends (direction indicated by the reference sign X in FIG. 1), the outer edge 4a of each of the side seal sections 4 created by the aforementioned cutting/separation has an arc shape that protrudes toward the inside of the outer cover 3 (fusion-bonded sheet article), a fusion-bonded section 40 where the four sheets 31, 32 constituting the outer cover 3 are fusion-bonded is formed in such a manner that the fusion-bonded section 40 includes the outer edge 4a of the side seal sections 4 and is located inwardly of the outer cover 3 (the fusion-bonded sheet article) from the outer edge 4a. In the thickness direction (the up-and-down direction in FIG. 6(*c*) or FIG. 7) of the outer cover 3, the width of the fusion-bonded section 40 is wider in the central section thereof than both end sections (upper and lower end sections). More specifically, in a cross-sectional view along the width direction of the diaper 1 (i.e., the direction orthogonal to the cutting/separating direction by the laser beam), the width of the fusion-bonded section 40 becomes gradually wider toward the central section thereof in the thickness direction, and the fusion-bonded section 40 is formed so as to have a crescent shape or half-moon shape (the fusion-bonded section 40 illustrated in FIG. 6(*c*) or FIG. 7 has a crescent shape).

The side seal section 4 includes the fusion-bonded section 40 which is formed by the melting and solidification of the sheet-forming materials, and thus, the side seal section 4 is a section that may deteriorate the comfortableness of wearing the diaper 1 because it is harder and has poor texture compared to other sections in the diaper 1. However, by forming the fusion-bonded section 40 in a crescent shape or half-moon shape in a cross-sectional view along the width direction of the diaper 1, it is possible to reduce the proportion of the fusion-bonded section 40 that exists at the corners 3S of the side edge section of the outer cover 3 constituting the side seal section 4, compared to cases where the fusion-bonded section's cross section has a rectangular shape as in conventional side seal sections. Thus, the softness and texture originally possessed by the corners 3S are less impaired, and thus, the comfortableness of wearing the diaper is improved compared to conventional diapers. On the other hand, a sufficient amount of fusion-bonded section 40 exists in the thickness-wise central section of the side edge section of the outer cover 3 (the section sandwiched between the corner 3S on the side of one surface of the outer cover 3 and the corner 3S on the side of the other surface), the thickness-wise central section being a section that greatly affects the fusion-bond strength of the side seal section 4. Thus, the side seal section 4 has a fusion-bond strength that is sufficient for practical use, and disadvantages, such as the tearing of the side seal section 4 while the diaper 1 is worn, are less prone to occur.

Figure 8A:
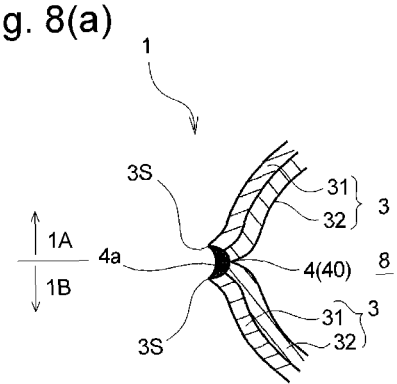
FIGS. 8(*a*) and 8(*b*) are diagrams corresponding to FIG. 3, each illustrating a side seal section (sealed edge section) on one side and the vicinity thereof in a state where the waist opening of the diaper illustrated in FIG. 3 is opened.
Figure 8B:
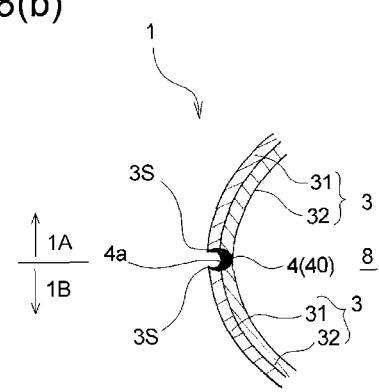

Another characteristic of the side seal section 4 (fusion-bonded section 40) is that the side seal section 4 is less visible from the outside in a state where the diaper 1 is worn or when it is in its natural state (contracted state). FIG. 8 illustrates the side seal section 4 (fusion-bonded section 40) in a state where the waist opening 8 is opened when the diaper 1 is worn. In a state where the waist opening 8 is opened, normally, the side seal section 4 is in a state where the fusion-bonded section 40 is exposed as illustrated in FIG. 8(a); however, because the outer edge 4a of the side seal section 4 has an arc shape that protrudes toward the inside of the outer cover 3 and because the present fusion-bonded section 40 is smaller compared to conventional side seal sections (fusion-bonded sections), the side seal section 4 is less visible from the outside. Particularly, because the outer edge 4a of the side seal section 4 has an arc shape that protrudes toward the inside of the outer cover 3, in a state where the waist opening 8 is opened when the diaper 1 is worn, there are cases where—depending on the materials for forming the sheets 31 and 32—the corner 3S of the side edge section of the outer cover 3 on the stomach-side section 1A side and the corner 3S of the side edge section of the outer cover 3 on the back-side section 1B side come close to one another, and the distance between the corners 3S is reduced, as illustrated in FIG. 8(b). Thus, the fusion-bonded section 40 located between the corners 3S becomes more difficult to touch with the hand and difficult to see from the outside owing to the corners 3S—which are located more toward the outside of the diaper 1 than the fusion-bonded section 40—that have come close to one another. Thus, not only the comfortableness of wearing the diaper 1, but also the outer appearance thereof is improved.

It should be noted that, if the side seal section 4 (fusion-bonded section 40) is difficult to see from the outside in a state where the diaper 1 is worn or when it is in its natural state (contracted state), then, for example, it may be hard for the parent (such as the mother) of a child, who is the wearer, to find the side seal section 4 when removing the diaper 1 after use thereof, and it may take time and effort for him/her to remove the diaper 1. An example of a means for overcoming such disadvantages caused by the decrease in visibility of the side seal sections 4 is a method of providing constituent members of the diaper 1 that cross over the side seal section 4 with different colors between the stomach side (front side) and the back side (rear side) with respect to the side seal section 4. More specifically, an example is a method of making the color of the waist section elastic members 5 or the outer cover 3 (outer layer sheet 31; inner layer sheet 32) in the stomach-side section 1A (front body section) of the diaper 1 different from the color thereof in the back-side section 1B (rear body section). According to this method, the side seal section 4 is located at a section where the colors change, and thus, the visibility of the side seal section 4 with the eye is improved, and the aforementioned disadvantages are prevented effectively.

It is surmised that the reason why the fusion-bonded section 40 of the side seal section 4 is formed in a crescent shape or half-moon shape in a cross-sectional view along the width direction of the diaper 1 is because the continuous diaper strip 10 (section-to-be-cut/separated 10C) made of nonwoven fabric is interposed and arranged between the support member 21 and the pressing member 24, which are made of metal materials, during and immediately after irradiation of the laser beam 30 with respect to the section-to-be-cut/separated 10C of the continuous diaper strip 10, as illustrated in FIGS. 6(b) and 6(c) (FIG. 7). That is, the metal materials, which are the main materials forming the support member 21 and the pressing member 24 sandwiching the continuous diaper strip 10 (outer layer sheet 31 and inner layer sheet 32) from above and below, have a higher thermal conductivity than the nonwoven fabric which is the main material forming the sheets 31, 32, and thus, the heat generated in the sheets 31, 32 by irradiation with the laser beam 30 is cooled by outside air, and simultaneously, is rapidly absorbed by the support member 21 or the pressing member 24 that contacts the sheets 31, 32. The corners 3S of the side edge section of the outer cover 3 constituting the side seal section 4 formed by cutting/separating the continuous diaper strip 10 by irradiation with the laser beam 30 are in contact with the support member 21 or the pressing member 24 having a higher thermal conductivity than the corners 3S, and so, the heat generated in the corners 3S is rapidly absorbed by the members 21, 24; as a result, the corners 3S are less prone to reach high temperatures at which fusion-bonded sections 40 are formed, and thus, the proportion of the fusion-bonded section 40 in the corner 3S is extremely low. On the other hand, the thickness-wise central section of the side edge section of the outer cover 3 (i.e., the central section of a section sandwiched between the corner 3S on the side of one surface of the outer cover 3 and the corner 3S on the side of the other surface) is not in contact with the members 21, 24 having a high thermal conductivity, and thus, the heat generated in the central section by irradiation with the laser beam 30 remains in the central section and makes the central section melt; as a result, a greater amount of fusion-bonded section 40 concentrates in the central section.

Thus, in order to form the fusion-bonded section 40 in a crescent shape or a half-moon shape in a cross-sectional view along the width direction of the diaper 1 and to achieve the aforementioned effects, it is preferable that, as in the present embodiment: the support member 21 and the pressing member 24 are made of a metal material, such as iron, aluminum, stainless steel, or copper, or a ceramic; and at least one sheet of the sheets (particularly, the outer layer sheet 31 forming the outer surface of the outer cover 3) of the plurality of sheets 31, 32 constituting the continuous diaper strip 10 (belt-shaped sheet laminate) partially includes a resin material, and more specifically, is made of a nonwoven fabric, for example. Furthermore, it is preferable that all of the plurality of sheets 31 include a resin material. As for the nonwoven fabric, any nonwoven fabric ordinarily used in this technical field can be used without particular limitation.

Further, from the viewpoint of reliably forming the fusion-bonded section 40 in a crescent shape or a half-moon shape in a cross-sectional view along the width direction of the diaper 1 (fusion-bonded sheet article) and providing the side seal sections 4 (sealed edge sections) with a sufficient fusion-bond strength for practical use, and also from the viewpoint of reducing the processing energy necessary for manufacturing the fusion-bonded sheet articles, the ratio ($\Phi$/W) of the diameter $\Phi$ of the laser beam 30's spot (i.e., section irradiated with the laser beam 30) on the continuous diaper strip 10 (belt-shaped sheet laminate) with respect to the width W of the slit-shaped opening 27 through which the laser beam 30 is emitted (cf. FIG. 6(b); the length of the opening 27 along the circumferential direction of the cylindrical roller 23) is: preferably 0.05 or greater, more preferably 0.1 or greater, even more preferably 0.4 or greater; and preferably 8 or less, more preferably 7 or less, even more preferably 2 or less; and more specifically, preferably 0.05 to 8, more preferably 0.1 to 7, even more preferably 0.4 to 2. The width W of the slit-shaped opening 27 is, for example, 0.1 to 4.0 mm As described above, the sections (sections-to-be-cut/separated 10C) in the continuous diaper strip 10 (sheet laminate) that overlap the openings 27 do not receive pressurizing force created by being sandwiched between the support member 21 and the pressurizing belt 24 (pressing member). The section 10C, however, is a section that is virtually affected by the pressurizing force, and thus, the fusion-bonded section 40 is formed. In order to form the fusion-bonded section 40 more stably, it is advantageous to devise a method for further increasing the pressurizing force created by the sandwiching between the members 21, 24.

Figure 9:
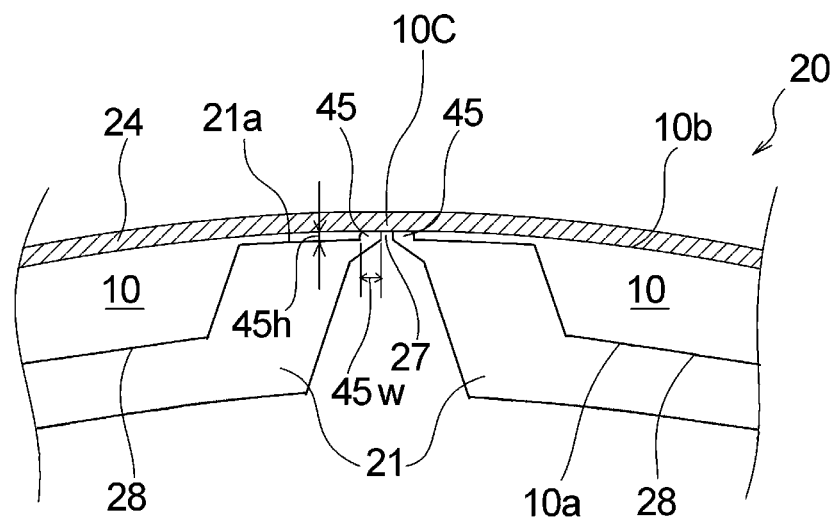
FIG. 9 is a schematic cross-sectional view of main parts of a modified example of the device illustrated in FIG. 1.

FIG. 9 illustrates a modified example in which a portion of the laser joining device 20 is improved in order to allow the fusion-bonded section 40 to be formed more stably. In the modified example illustrated in FIG. 9, a protruding section 45 is formed in the vicinity of the slit-shaped opening 27 (a region within 35 mm from the edge section of the opening 27) on the outer surface 21a of the support member 21 where the continuous diaper strip 10 is arranged, the protruding section 45 protruding more toward the continuous diaper strip 10 arranged on the outer surface 21a (more toward the pressurizing belt 24) than peripheral sections of the opening 27. More specifically, a protruding section 45 is formed on the outer surface 21a of the support member 21 at each opening edge section of a pair of opening edge sections that flank each opening 27 and that extend along the opening's length direction (the width direction of the support member 21). Each protruding section 45 is continuous along the opening 27 over the entire length in the opening's length direction, and is rectangular in a planar view. The protrusion height 45h of each protruding section 45 (the height of protrusion from peripheral sections) is constant and does not change over the entire length of the protruding section 45. The top section of the protruding section 45 may be flat, or may be a curved surface having a predetermined curvature, and the curved surface may be parallel to the outer surface 21a of the cylindrical support member 21.

By forming protruding sections 45 in the vicinity (opening edge sections) of the opening 27 on the outer surface 21a of the support member 21 and thereby providing a step between the vicinity of the opening 27 and the peripheral sections thereof, the vicinity of the section-to-be-cut/separated in the continuous diaper strip 10 will be located at the top section of each protruding section 45, which is at a relatively high position in the aforementioned step; thus, the pressurizing force applied to a section corresponding to the vicinity of the opening will be increased in a localized manner. Thus, the aforementioned pressurizing force on the continuous diaper strip 10 is effectively prevented from decreasing in a localized manner, and melting/cutting of the continuous diaper strip 10 will be performed even more stably, thus further increasing the fusion-bond strength of the side seal sections 4 (sealed edge sections) in the final diaper 1 (fusion-bonded sheet article).

From the viewpoint of achieving the aforementioned effect more reliably, the protrusion height 45h of the protruding section 45 (cf. FIG. 9) is: preferably 0.1 mm or greater, more preferably 1 mm or greater; and preferably 10 mm or less, more preferably 8 mm or less; and more specifically, preferably from 0.1 mm to 10 mm inclusive, more preferably from 1 mm to 8 mm inclusive.

The width 45w of the protruding section 45 (cf. FIG. 9; the length in a direction orthogonal to the width direction of the support member 21) is: preferably 1 mm or greater, more preferably 2 mm or greater; and preferably 20 mm or less, more preferably 10 mm or less; and more specifically, preferably from 1 mm to 20 mm inclusive, more preferably from 2 mm to 10 mm inclusive.

Figure 10:
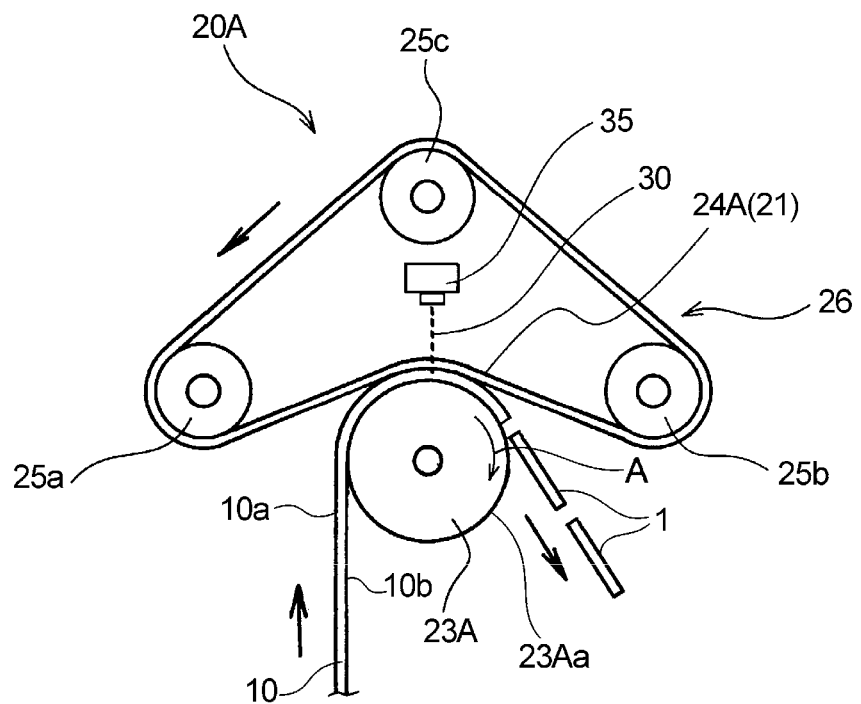
FIG. 10 is a diagram illustrating another modified example of the device illustrated in FIG. 1.

FIG. 10 illustrates another modified example of the laser joining device illustrated in FIG. 1. The following description regarding this modified example mainly focuses on constituent parts that are different from those in the aforementioned laser joining device 20, and similar constituent parts are accompanied by the same reference signs and explanation thereof is omitted. The explanation on the aforementioned laser joining device 20 applies as appropriate to constituent parts that are not particularly explained.

The laser joining device 20 illustrated in FIG. 1 is configured in such a manner that a laser beam 30 is emitted from an irradiation head 35 provided in a hollow section of a hollow cylindrical roller 23 toward a support member 21 forming the peripheral surface section of the cylindrical roller 23. In contrast, the laser joining device 20A illustrated in FIG. 10 is configured in such a manner that a laser beam 30 is emitted from an irradiation head 35 provided in a space surrounded by a pressurizing belt 24A of a belt-type pressurizing device 26 toward the pressurizing belt 24A. More specifically, the laser joining device 20A includes a cylindrical roller 23A (pressing member) that is driven to rotate in the direction of arrow A, and a belt-type pressurizing device 26 provided with an endless pressurizing belt 24A, wherein the cylindrical roller 23A serves as the pressing member, and the pressurizing belt 24A serves as the support member 21 having light passage sections (not illustrated) through which a laser beam 30 can pass. The cylindrical roller 23A is solid and cylindrical (annular), and its peripheral surface section 23Aa is flat and smooth. Each light passage section (not illustrated) in the pressurizing belt 24A (support member 21) is a slit-shaped opening that is rectangular in a planar view, like the opening 27 in the support member 21 (the peripheral surface section of the cylindrical roller 23) in the aforementioned laser joining device 20. The length direction of each opening matches the width direction of the pressurizing belt 24A (the direction parallel to the rotation axis of each of the three rollers 25a, 25b, 25c over which the pressurizing belt 24A is looped), and a plurality of the openings are formed with predetermined intervals therebetween in the length direction of the pressurizing belt 24A. A member similar to the support member 21 in the aforementioned laser joining device 20 may be used as the present cylindrical roller 23A (pressing member). A member similar to the pressurizing belt 24 serving as the pressing member in the aforementioned laser joining device 20 may be used as the present pressurizing belt 24A (support member 21).

In the method for manufacturing pull-on disposable diapers by using the laser joining device 20A, as illustrated in FIG. 10, a continuous diaper strip 10 is introduced, by guide rollers (not illustrated) etc., onto the peripheral surface section 23Aa of the cylindrical roller 23A (pressing member) in such a manner that the other surface 10b abuts against the peripheral surface section 23Aa, and, while the continuous diaper strip 10 is continuously transported so as to be wrapped around the cylindrical roller 23A, one surface 10a thereof is made to abut against the outer surface of the pressurizing belt 24A (support member 21)—which has slit-shaped openings (not illustrated; light passage sections) through which the laser beam 30 can pass—whereas the other surface 10b thereof is pressed against the peripheral surface section 23Aa of the cylindrical roller 23A, and, by irradiating the continuous diaper strip 10, which is in this (pressurized) state, with the laser beam 30 from the pressurizing belt 24A side via the opening, the continuous diaper strip 10 is cut and separated and, simultaneously, the cut edge sections, which have been created by the cutting and separation, in the plurality of sheets in the aforementioned pressurized state are fusion-bonded together. Thus, pull-on disposable diapers 1 (fusion-bonded sheet articles) each including an outer cover 3 (fusion-bonded sheet article) having a pair of side seal sections 4, 4 (sealed edge sections) are manufactured continuously (cf. FIG. 2).

The laser beam employed in the present invention (first invention) will be described. A laser beam having a wavelength that is absorbed by the sheet(s) constituting the sheet laminate and that causes the sheet(s) to generate heat is employed as the laser beam to be emitted onto the sheet laminate. Here, "the sheet constituting the sheet laminate" is not limited to the sheet (e.g., the outer layer sheet 31 in the aforementioned embodiment) constituting one surface (the surface abutting against the support member) of the sheet laminate, but it may be any sheet constituting the sheet laminate. Whether or not the laser beam emitted onto the sheet laminate has a wavelength that is absorbed by each sheet constituting the sheet laminate and that causes that sheet(s) to generate heat is determined by the relationship between the sheet material and the wavelength of the laser beam used. In cases where the sheet constituting the sheet laminate is a synthetic-resin-made nonwoven fabric or film that is generally used in the manufacture of absorbent articles (sanitary products) such as disposable diapers and sanitary napkins as in the foregoing embodiment, it is preferable to use laser beams such as $CO_2$ lasers, YAG lasers, LD lasers (semiconductor lasers), YVO4 lasers, or fiber lasers. In cases where the sheet constituting the sheet laminate includes, for example, polyethylene, polyethylene terephthalate, or polypropylene as synthetic resin, it is preferable to employ a wavelength range of, for example, 8.0 to 15 μm as wavelengths that can be absorbed by the sheet and cause the sheet to generate heat satisfactorily. It is more preferable if the oscillation wavelength of a $CO_2$ laser where a high-power laser device exists is 9.0 to 11.0 μm. The spot diameter of the laser beam, the laser output, etc., can be chosen as appropriate with consideration given to the material, thickness, etc., of the sheets constituting the sheet laminate.

The fusion-bonded sheet article manufactured in the present invention (first invention) may be used as-is, or may be integrated with other components and used as various articles. Examples of various articles include: various absorbent articles, such as sanitary napkins and incontinence pads, in addition to the aforementioned pull-on disposable diapers; and articles other than absorbent articles, such as sheets for cleaning floor surfaces, sheets for wiping the body, and heat generators for warming the body. Examples of fusion-bonded sheet articles constituting absorbent articles include: (a) an article in which a topsheet forming a skin-contacting surface of an absorbent article and a backsheet forming a skin-non-contacting surface of the absorbent article are joined together in sections extending outward from the peripheral edge of an absorbent core; and (b) a sanitary napkin made by fusion-bonding a topsheet and a wing-section forming sheet of the sanitary napkin, or the wing-section forming sheet and a backsheet, or the topsheet, the wing-section forming sheet, and the backsheet. An example of a fusion-bonded sheet article constituting a heat generator for warming the body is a heat generator employing heat generation involving an oxidation reaction between oxygen in air and an oxidizable metal, the heat generator being configured in such a manner that a sheet-faun heat-generating element is interposed and arranged between two air-permeable sheets, wherein the sheet-form heat-generating element generally includes an oxidizable metal, an electrolyte, and water.

Particularly, because the fusion-bonded sheet article manufactured by the present invention has sealed edge sections that are soft and have a pleasant texture, in cases where the absorbent article is a sanitary napkin, the fusion-bonded sheet article manufacturing step may be employed for forming an outer-peripheral seal section by joining a topsheet and a backsheet, with an absorbent core interposed therebetween, along the outer periphery of the sanitary napkin. Further, the fusion-bonded sheet article manufacturing step may be employed for forming an outer-peripheral seal section by joining a topsheet and a backsheet, with an absorbent core interposed therebetween, along the outer periphery of the main body part (the part excluding the wings) of the sanitary napkin.

Incidentally, the light passage section of the foregoing embodiment is a slit-shaped opening that penetrates the support member in the thickness direction, like the opening 27 illustrated in FIG. 6(*b*). The light passage section of the present invention, however, is not limited thereto, and, as illustrated in FIG. 11(*a*) for example, the vicinity of an end (outer edge) 21*s* of the support member 21 (i.e., a section where the support member does not exist) may be employed as the light passage section. In this case, the sheet laminate 10 (continuous diaper strip) includes a section 10A sandwiched between the support member 21 and the pressurizing belt 24 (pressing member), and a section 10B that does not abut against the support member 21, and the sandwiched section 10A and the vicinity thereof are in a state where they are pressurized (compressed) in the thickness direction before being cut and separated by the laser beam irradiation, whereas a section within the aforementioned section 10B excluding the vicinity of the sandwiched section 10A (i.e., a section that is equal to or more than a predetermined distance away from the end 21*s* of the support member 21) is in a non-pressurized (non-compressed) state. If, as illustrated in FIG. 11(*a*), the sheet laminate 10 in this one-side pressurized state—wherein pressurization takes place only on one side with respect to the section irradiated with the laser beam—is irradiated with the laser beam 30 at the vicinity of the end 21*s* of the support member 21 and the continuous diaper strip 10 is cut and separated into the sandwiched section 10A and the non-abutting section 10B, the cut edge sections of the sheets in the sandwiched section 10A are fusion-bonded because they are in a pressurized state before the cutting/separation, but the cut edge sections of the sheets in the non-abutting section 10B are not fusion-bonded because they are in a non-pressurized state before the cutting/separation. Herein, the "vicinity of an end (outer edge) 21*s* of the support member 21" is a region in which the sheet laminate 10 (continuous diaper strip) is in a pressurized state by the support member 21, and more specifically, is a region preferably within 2 mm, more preferably within 1 mm, from the end 21*s* of the support member 21.

As illustrated in FIG. 11(*a*), in cases where the light passage section is the vicinity of an end 21*s* of the support member 21 and the sheet laminate 10 (continuous diaper strip) in a one-side pressurized state is irradiated with a laser beam 30 via the aforementioned light passage section and is cut and separated, from the viewpoint of reliably forming the fusion-bonded section 40 in a crescent shape or a half-moon shape in a cross-sectional view along the width direction of the fusion-bonded sheet article (diaper 1) and providing the side seal sections 4 (sealed edge sections) with a sufficient fusion-bond strength for practical use, and also from the viewpoint of reducing the processing energy necessary for manufacturing the fusion-bonded sheet articles, the ratio ($\Phi$/W') of the diameter $\Phi$ of the laser beam 30's spot (section irradiated with the laser beam 30) on the sheet laminate 10 with respect to the distance W' from the end 21s of the support member 21 to the center of the laser beam 30's spot is: preferably 0.1 or greater, more preferably 0.2 or greater, even more preferably 0.8 or greater; and preferably 16 or less, more preferably 14 or less, even more preferably 8 or less; and more specifically, preferably 0.1 to 16, more preferably 0.2 to 14, even more preferably 0.8 to 8.

Figure 11A:
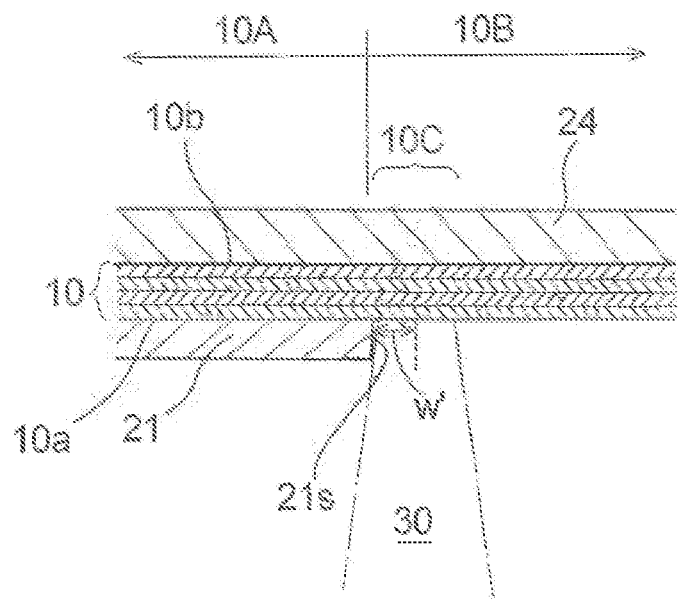
FIGS. 11(*a*) and 11(*b*) are diagrams (corresponding to FIG. 6(*b*)), illustrating modified examples of main parts in the device illustrated in FIG. 1.
Figure 12:
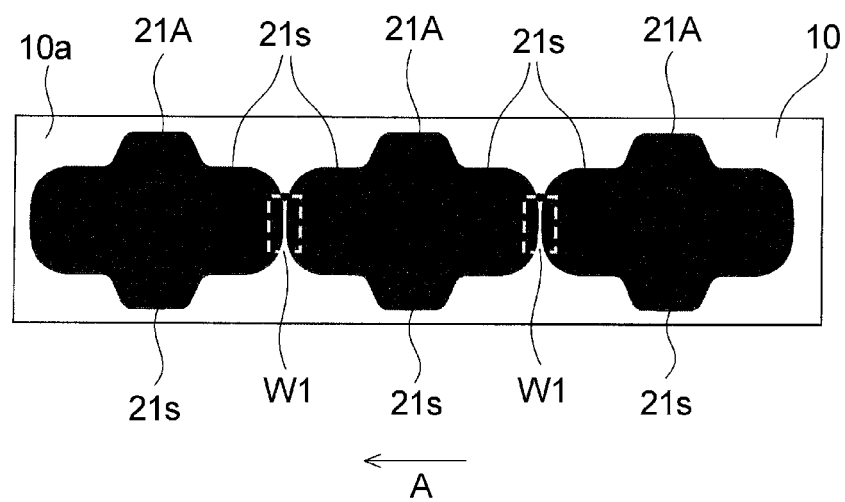
FIG. 12 is a schematic plan view (plan view from the side of a surface of a sheet laminate abutting against a support member) of an example of a method for manufacturing sanitary napkins by using a laser joining device, which is another embodiment of an absorbent article manufacturing method of the present invention.

FIG. 12 illustrates an embodiment of a method for manufacturing sanitary napkins, as an example of employing the embodiment of irradiating a belt-shaped sheet laminate in the so-called one-side pressurized state with a laser beam as illustrated in FIG. 11(a). In the sanitary napkin manufacturing method illustrated in FIG. 12: a belt-shaped sheet laminate 10 is transported in the direction of arrow A while making one surface 10a thereof abut against support members 21A; a pressing member (not illustrated), such as a pressurizing belt 24 (cf. FIG. 1) is pressed against the other surface (not illustrated) of the sheet laminate 10; and the belt-shaped sheet laminate 10 in this state is irradiated with a laser beam via a light passage section from the support member 21A side. The planar-view shape of each support member 21A is the same as the planar-view shape of a sanitary napkin, which is the intended product, and a plurality of support members 21A are arranged at predetermined intervals W1 in the transporting direction A, with the length direction of each support member 21A matching the transporting direction A of the sheet laminate 10. While the belt-shaped sheet laminate 10 is made to abut against the thus-arranged support members 21A, the belt-shaped sheet laminate 10 is irradiated with a laser beam along the end (outer edge) 21s of each support member 21 from the support member 21A side, and thereby, a single piece of sanitary napkin (or a precursor thereof) can be isolated from the belt-shaped sheet laminate 10. In this case, the interval W1 (the section surrounded by dotted lines in FIG. 12) between two support members 21A, 21A adjacent to one another in the transporting direction A functions as the light passage section, like the opening 27 illustrated in FIG. 5; the cut edge sections of the sheets on one side of the interval W1 in the transporting direction A, as well as the cut edge sections of the sheets on the other side of the interval, are fusion-bonded because they are in a pressurized state before the cutting/separation by being sandwiched between the support members 21A and the pressing member (not illustrated). In contrast, sections, of the belt-shaped sheet laminate 10, that are in the vicinity of the ends 21s of each support member 21A but where the interval W1 is not formed (i.e., sections where the end 21 s of another support member 21A does not exist in the vicinity) are in the one-side pressurized state as illustrated in FIG. 11(a). Thus, in a planar view as illustrated in FIG. 12, the cut edge sections of the sheets on the side overlapping the support member 21A are fusion-bonded because they are in a pressurized state before the cutting/separation, but the cut edge sections on the side that does not overlap the support member 21A are not fusion-bonded because they are in a non-pressurized state before the cutting/separation. In a single piece of sanitary napkin isolated as above, the plurality of sheets constituting the sanitary napkin (sheet laminate 10) are fusion-bonded (joined) together in the outer periphery of the sanitary napkin, and an outer-peripheral seal section is formed.

Figure 11B:
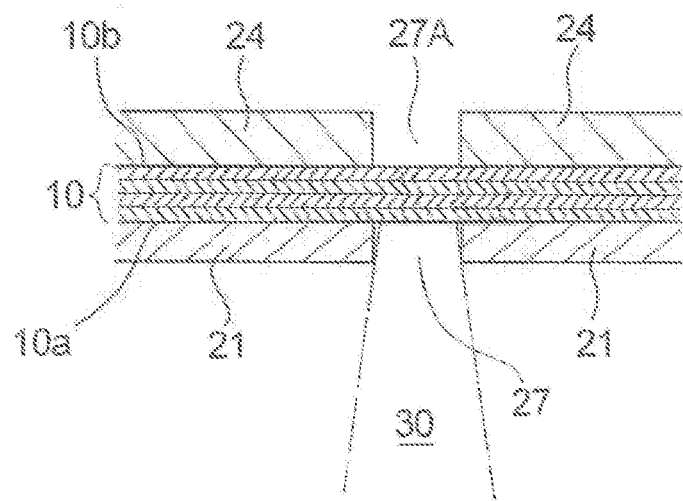

Further, as illustrated in FIG. 11(b), the pressurizing belt 24 (cf. FIG. 6(b)) serving as the pressing member in the foregoing embodiment may have openings 27A at sections corresponding to the openings 27 (light passage sections) in the support member 21. The openings 27A have the same planar-view shape and dimensions as the opening 27. By providing openings 27A in the pressing member in a section opposing the opening 27 (light passage section) across the sheet laminate 10, various effects can be expected, such as: the efficient elimination of gases generated by laser beam irradiation; the prevention of contamination of the pressing member; the suppression of overheating of the pressing member; the promotion of cooling of the pressing member; and the promotion of cooling of the fusion-bonded section 40. When the belt-shaped sheet laminate 10 is irradiated with a laser beam 30 via the opening 27 and is cut and separated, the cut edge sections of the sheets on one side of the opening 27, as well as the cut edge sections of the sheets on the other side of the opening, are fusion-bonded because they are in a pressurized state before the cutting/separation, as illustrated in FIG. 11(b). The cylindrical roller 23A (pressing member) illustrated in FIG. 10 may have, in its peripheral surface section 23Aa, an opening that has the same planar-view shape and dimensions as the aforementioned not-illustrated opening (light passage section) in the pressurizing belt 24A (support member 21) in a section corresponding to the opening (light passage section).

The present invention (first invention) has been described above according to embodiments thereof, but the present invention is not limited to the foregoing embodiments and may be modified as appropriate within a scope that does not depart from the gist of the present invention. For example, the sheet laminate may be made by layering two, three, or five or more sheets, instead of four sheets as illustrated in FIG. 6(a). Further, in order to wrap the continuous diaper strip 10 (sheet laminate) around the cylindrical roller 23 (support member 21) without causing any wrinkles or slack, the laser joining device 20 may be provided with a mechanism for controlling the tension of the continuous diaper strip 10. The laser joining device 20 may also be provided with a mechanism for removing resin, etc., adhering to the pressing member 24's surface abutting against the continuous diaper strip 10. Further, in the foregoing embodiment, the step of forming sealed edge sections is executed on a cylindrical roller, but other than the cylindrical roller, this step may be executed on a discretionarily-formed curved surface or on a flat surface. Furthermore, the pressurizing means (pressurizing method) for bringing the continuous diaper strip 10 into a pressurized state is not limited to sandwiching the continuous diaper strip 10 between the support member 21 and the pressurizing belt 24 (pressing member) as described above, and other means/methods are possible, such as: sucking the continuous diaper strip 10 from the support member 21 side; blowing air onto the continuous diaper strip 10 from the opposite side from the support member 21 (i.e., from the pressing member side); adjusting the tension of the continuous diaper strip 10 onto the support member 21; and pressurizing by employing static electricity or magnetic force. Features provided in only one of the foregoing embodiments may all be used interchangeably among embodiments as appropriate.

In relation to the foregoing embodiments of the present invention (first invention), the following additional remarks (methods for manufacturing fusion-bonded sheet articles; fusion-bonded sheet articles; methods for manufacturing absorbent articles) are disclosed.

<1>
A method for manufacturing a fusion-bonded sheet article that includes sealed edge sections made by fusion-bonding edge sections of a plurality of sheets in a state where the sheets' edge sections are superposed, wherein:

at least one sheet of the plurality of sheets includes a resin material; and the manufacturing method comprises a step of forming the sealed edge sections by making one surface of a belt-shaped sheet laminate in which the plurality of sheets are laminated abut against a support member that has a light passage section through which a laser beam can pass, and irradiating, from the support member side via the light passage section, the belt-shaped sheet laminate, which is in a pressurized state, with a laser beam having a wavelength that is absorbed by the sheets constituting the sheet laminate and that causes the sheets to generate heat, and thus cutting and separating the belt-shaped sheet laminate and, simultaneously, fusion-bonding cut edge sections created, by the cutting/separation, in the plurality of sheets which are in the pressurized state.

<2>
The fusion-bonded sheet article manufacturing method as set forth in clause <1>, wherein the light passage section is a slit-shaped opening that penetrates the support member in its thickness direction.

<3>
The fusion-bonded sheet article manufacturing method as set forth in clause <2>, wherein the ratio ($\Phi$/W) of the diameter $\Phi$ of the laser beam's spot on the sheet laminate with respect to the width W of the slit-shaped opening is from 0.05 to 8 inclusive.

<4>
The fusion-bonded sheet article manufacturing method as set forth in clause <2>, wherein the ratio ($\Phi$/W) of the diameter $\Phi$ of the laser beam's spot on the sheet laminate with respect to the width W of the slit-shaped opening is preferably 0.05 or greater, more preferably 0.1 or greater, even more preferably 0.4 or greater, and preferably 8 or less, more preferably 7 or less, even more preferably 2 or less, and more specifically, preferably 0.05 to 8, more preferably 0.1 to 7, even more preferably 0.4 to 2.

<5>
The fusion-bonded sheet article manufacturing method as set forth in clause <2> or <3>, wherein a protruding section is formed in a vicinity of the opening on an outer surface of the support member where the sheet laminate is arranged, the protruding section protruding more toward the sheet laminate arranged on the outer surface than peripheral sections of the opening.

<6>
The fusion-bonded sheet article manufacturing method as set forth in clause <1>, wherein: the light passage section is a vicinity of an end of the support member; and the ratio ($\Phi$/W') of the diameter $\Phi$ of the laser beam's spot on the sheet laminate with respect to the distance W' from the end of the support member to the center of the laser beam's spot is from 0.1 to 16 inclusive.

<7>
The fusion-bonded sheet article manufacturing method as set forth in clause <1>, wherein: the light passage section is a vicinity of an end of the support member; and the ratio ($\Phi$/W') of the diameter $\Phi$ of the laser beam's spot on the sheet laminate with respect to the distance W' from the end of the support member to the center of the laser beam's spot is preferably 0.1 or greater, more preferably 0.2 or greater, even more preferably 0.8 or greater, and preferably 16 or less, more preferably 14 or less, even more preferably 8 or less, and more specifically, preferably 0.1 to 16, more preferably 0.2 to 14, even more preferably 0.8 to 8.

<8>
The fusion-bonded sheet article manufacturing method as set forth in any one of clauses <1> to <7>, wherein: at least one sheet of the plurality of sheets includes a heat-fusible synthetic resin and is, for example, a nonwoven fabric, a film, or a laminate sheet made of a nonwoven fabric and a film; and preferably, all of the plurality of sheets include a resin material.

<9>
The fusion-bonded sheet article manufacturing method as set forth in any one of clauses <1> to <8>, wherein: a pressing member is pressed against the other surface of the belt-shaped sheet laminate abutting against the support member; and the belt-shaped sheet laminate in this state is irradiated with the laser beam from the support member side via the light passage section.

<10>
The fusion-bonded sheet article manufacturing method as set forth in clause <9>, wherein the support member and the pressing member are made of a material selected from a metal material, a resin, or a ceramic.

<11>
The fusion-bonded sheet article manufacturing method as set forth in clause <9> or <10>, wherein:

the sheet laminate is in a one-side pressurized state;

the sheet laminate in the one-side pressurized state includes a section sandwiched between the support member and the pressing member, and a section that does not abut against the support member; and the sandwiched section and the vicinity thereof are in a state where they are pressurized (compressed) in the thickness direction before being cut and separated by the laser beam irradiation, and a section within the section not abutting the support member and excluding the vicinity of the sandwiched section (i.e., a section that is equal to or more than a predetermined distance away from the end of the support member) is in a non-pressurized (non-compressed) state.

<12>
The fusion-bonded sheet article manufacturing method as set forth in clause <11>, wherein, if the sheet laminate in the one-side pressurized state is irradiated with a laser beam and the sheet laminate is cut and separated into the section sandwiched between the support member and the pressing member and the section that does not abut against the support member, the cut edge sections of the sheets in the sandwiched section are fusion-bonded because they are in a pressurized state before the cutting/separation, but the cut edge sections of the sheets in the section not abutting the support member are not fusion-bonded because they are in a non-pressurized state before the cutting/separation.

<13>
The fusion-bonded sheet article manufacturing method as set forth in clause <11> or <12>, wherein the sheet laminate in the one-side pressurized state is irradiated with a laser beam via the light passage section, and thus the sheet laminate is cut and separated.

<14>
A fusion-bonded sheet article manufactured by the manufacturing method according to any one of claims 1 to 18, wherein:

in a cross-sectional view along a direction orthogonal to the direction in which the sealed edge sections extend, an outer edge of each of the sealed edge sections created by the cutting/separation has an arc shape that protrudes toward the inside of the fusion-bonded sheet article; a fusion-bonded section where the sheets constituting the fusion-bonded sheet article are fusion-bonded is formed in such a manner that the fusion-bonded section includes the outer edge of the sealed edge section and is located inwardly of the fusion-bonded sheet article from the outer edge; and, in the thickness direction of the fusion-bonded sheet article, the width of the fusion-bonded section is wider in a central section thereof than both end sections thereof.

<15>

The fusion-bonded sheet article as set forth in clause <14>, wherein the fusion-bonded section, in its cross-sectional view, is formed so as to have a crescent shape or a half-moon shape.

<16>

A method for manufacturing an absorbent article, the method comprising a step of manufacturing a fusion-bonded sheet article by the manufacturing method as set forth in any one of clauses <1> to <13>.

<17>

The absorbent article manufacturing method as set forth in clause <16>, wherein:

the absorbent article is a pull-on disposable diaper including an absorbent assembly, and an outer cover that is arranged on a skin-non-contacting surface side of the absorbent assembly and to which the absorbent assembly is fixed, wherein a pair of side seal sections are formed by joining both side edge sections of the outer cover in a stomach-side section and both side edge sections of the outer cover in a back-side section; and the fusion-bonded sheet article is made by folding a belt-shaped outer cover in its width direction, and irradiating a predetermined section of the folded outer cover with the laser beam, and thus, cutting and separating the belt-shaped outer cover and, simultaneously, forming the side seal section.

<18>

The absorbent article manufacturing method as set forth in clause <17>, the manufacturing method comprising a step of feeding a belt-shaped outer layer sheet and a belt-shaped inner layer sheet between a pair of nip rollers and pressurizing the sheets, and thus forming the belt-shaped outer cover in which a plurality of elastic members are arranged in their stretched state between the two sheets.

<19>

The absorbent article manufacturing method as set forth in clause <17>, the manufacturing method comprising a step of feeding a belt-shaped outer layer sheet and a belt-shaped inner layer sheet, with waist section elastic members, hip section elastic members, and leg section elastic members sandwiched therebetween in their stretched state, between a pair of nip rollers and pressurizing the sheets, and thus forming the belt-shaped outer cover in which a plurality of elastic members are arranged in their stretched state between the two sheets.

<20>

The absorbent article manufacturing method as set forth in any one of clauses <16> to <19>, wherein, at the time of cutting and separating a continuous absorbent-article strip into separate pieces by the laser beam irradiation, two mutually-superposed sheets in a section-to-be-cut/separated of the continuous absorbent-article strip, and the vicinity thereof, are joined by an adhesive, etc., prior to the laser beam irradiation.

<21>

The absorbent article manufacturing method as set forth in any one of clauses <16> to <20>, wherein, after the termination of the laser beam irradiation, the sheets' cut edge sections created by the cutting/separation by the laser beam irradiation are cooled by contacting the support member and solidify, and thus, the cut edge sections are made into a fusion-bonded section in which the materials (fibers, etc.) forming the cut edge sections are molten and integrated together.

<22>

The absorbent article manufacturing method as set forth in any one of clauses <16> to <21>, wherein the absorbent article is an article in which a topsheet forming a skin-contacting surface of the absorbent article and a backsheet forming a skin-non-contacting surface of the absorbent article are joined together in sections extending outward from a peripheral edge of an absorbent core.

<23>

The absorbent article manufacturing method as set forth in any one of clauses <16> to <21>, wherein the absorbent article is a sanitary napkin, and is made by fusion-bonding: a topsheet and a wing-section forming sheet of the sanitary napkin; or the wing-section forming sheet and a backsheet; or the topsheet, the wing-section forming sheet, and the backsheet.

<24>

An absorbent article including an absorbent assembly, and an outer cover that is arranged on a skin-non-contacting surface side of the absorbent assembly and to which the absorbent assembly is fixed, wherein a pair of side seal sections are formed by joining both side edge sections of the outer cover in a stomach-side section and both side edge sections of the outer cover in a back-side section, wherein:

each side seal section is formed by folding a belt-shaped outer cover in its width direction, and irradiating a predetermined section of the folded outer cover with a laser beam, and thus, cutting and separating the belt-shaped outer cover and, simultaneously, forming the side seal section; and an outer edge of each side seal section has an arc shape that protrudes toward the inside of the outer cover.

<25>

The absorbent article as set forth in clause <24>, wherein: each side seal section includes a fusion-bonded section which is formed by the melting and solidification of sheet-forming materials; and the fusion-bonded section is formed so as to have a crescent shape or a half-moon shape in a cross-sectional view along the width direction of the absorbent article.

<26>

The absorbent article as set forth in clause <24> or <25>, wherein: the absorbent article has a waist opening; and, in a state where the waist opening is opened when the absorbent article is worn, a corner of the side edge section of the outer cover on the stomach-side section side and a corner of the side edge section of the outer cover on the back-side section side come close to one another, and the distance between the corners is reduced.

<27>

The absorbent article as set forth in any one of clauses <24> to <26>, wherein: the absorbent article includes waist section elastic members forming waist gathers; and the color of the waist section elastic members in the stomach-side section (front body section) is different from the color of the waist section elastic members in the back-side section (rear body section).

<28>
The absorbent article as set forth in any one of clauses <24> to <27>, wherein the color of the outer cover (outer layer sheet; inner layer sheet) in the stomach-side section (front body section) is different from the color of the outer cover in the back-side section (rear body section).

<29>
A laser joining device used in the manufacturing method as set forth in any one of clauses <1> to <13>, wherein:
the laser joining device comprises a hollow cylindrical roller provided with a cylindrical support member that is driven to rotate, a belt-type pressurizing device provided with an endless pressurizing belt, and an irradiation head arranged in a hollow section of the cylindrical roller and emitting a laser beam toward the support member which forms a peripheral surface section of the cylindrical roller; and
the cylindrical roller has a slit-shaped opening that penetrates the support member in its thickness direction.

<30>
A laser joining device used in the manufacturing method as set forth in any one of clauses <1> to <13>, wherein:
the laser joining device includes a cylindrical roller that is driven to rotate, a belt-type pressurizing device provided with an endless pressurizing belt, and an irradiation head that emits a laser beam and that is arranged in a space surrounded by the pressurizing belt of the belt-type pressurizing device; and
the pressurizing belt has a slit-shaped opening that is rectangular in a planar view.

<31>
The laser joining device as set forth in clause <30>, wherein the endless pressurizing belt moves at the same speed as the cylindrical roller.

EXAMPLES

The present invention (first invention) will be described in further detail below according to Examples thereof. Note, however, that the present invention is not limited to the following Examples.

Example 1

A fusion-bonded sheet article having sealed edge sections was manufactured by irradiating a sheet laminate with a laser beam according the aforementioned method. The following three types of sheet laminates 1 to 3 were used as the sheet laminate. The laser joining device used basically had the same configuration as the laser joining device 20 illustrated in FIG. 1, except that the laser beam was emitted onto the sheet laminate in its standstill state. In the laser joining device: the support member 21 was made of a 2-mm-thick stainless steel (SUS 304); the pressing member 24 was made of a 0.75-mm-thick stainless steel (SUS 304H); the width W (cf. FIG. 6(*b*)) of the slit-shaped opening 27 (light passage section) in the support member was 0.5 mm; the pressurizing force (surface pressure) on the sheet laminate by the support member 21 and the pressurizing member 24 was 150 kPa; and the length of the pressurized section along the cutting/separating direction by the laser beam (the width direction of the sheet laminate) was 200 mm. A $CO_2$ laser was employed as the laser beam, and the laser output was 24 W. The laser beam scanning speed was varied in such a manner that the energy density D (unit: $J/mm^2$) in the region irradiated with the laser beam became constant. The energy density D is a value found by dividing the energy of the irradiated laser beam by the area of the irradiated region, and is calculated by the following Formula (1A). In Formula (1A), P is the laser output (W), Φ is the diameter (mm) of the laser beam's spot on the sheet laminate, and v is the laser beam scanning speed (mm/s). The energy density D was varied depending on the type of sheet laminate, and was 0.40 $J/mm^2$ for the sheet laminates 1 and 2 and was 0.80 $J/mm^2$ for the sheet laminate 3. As is clear from the following Formula (1A), the energy density D changes in accordance with the change in the diameter Φ of the laser beam's spot, and so, the energy density D was kept constant by changing, as appropriate, the laser beam scanning speed. The laser beam scanning speed was 300 mm/s, 59 mm/s, and 14 mm/s, respectively, when the diameter Φ of the spot on the sheet laminate 1 or 2 was changed between 0.20 mm, 1.00 mm, and 3.50 mm, and the scanning speed was 150 mm/s, 29 mm/s, and 6 mm/s, respectively, when the diameter of the spot on the sheet laminate 3 was changed between 0.20 mm, 1.00 mm, and 3.50 mm.

[Math. 1]

$$D = \frac{4P}{4v\phi + \pi\phi^2} \tag{1A}$$

Sheet Laminate 1: Sheet laminate 1 was a laminate made by laminating four spun-bonded nonwoven fabrics, each made of polypropylene synthetic fibers and having a basis weight of 18 $g/m^2$, and fixing thread-shaped elastic members with a hot-melt adhesive between the first and second sheets and between the third and fourth sheets. In the sheet laminate 1, the basis weight of application of the hot-melt adhesive was 15 $g/m^2$, and a plurality of elastic members were fixed in such a manner that the length direction of the elastic members matched the length direction of the sheet laminate 1, at 6-mm intervals therebetween in the width direction of the sheet laminate 1 (i.e., the cutting/separating direction by the laser beam) which is orthogonal to the length direction.

Sheet Laminate 2: Sheet laminate 2 was a laminate having a similar structure to the sheet laminate 1, except that no elastic members were used and only the hot-melt adhesive was applied.

Sheet Laminate 3: Sheet laminate 3 was a laminate made by laminating two transparent polyethylene films each having a basis weight of 3.9 $g/m^2$.

Examples 2-4 and Reference Example 1

Same as Example 1, except that the width W of the slit-shaped opening 27 (light passage section) and the diameter Φ of the laser beam's spot were changed as appropriate.

Example 5

Same as Example 1, except that the laser beam was emitted onto a belt-shaped sheet laminate in a one-side pressurized state, as illustrated in FIG. 11(*a*).

Example 6

Same as Example 1, except for using a pressurizing belt 24 (pressing member) that has openings 27A in a section corresponding to the opening 27 (light passage section) in the support member 21, as illustrated in FIG. 11(*b*).

Comparative Example 1

The laser beam was emitted onto a sheet laminate in a non-pressurized state.

{Evaluation}

The fusion-bonding property and fusion-bond strength of each sheet laminate (fusion-bonded sheet article) after laser beam irradiation were evaluated according to the methods described below. The results are shown in Table 1 below. It should be noted that, as for the Examples, in a cross-sectional view along a direction (the length direction of the sheet laminate) orthogonal to the direction in which the fusion-bonded sections extend (i.e., the cutting/separating direction by the laser beam, or the width direction of the sheet laminate), each fusion-bonded section (sealed edge section) in each sheet laminate (fusion-bonded sheet article) after laser beam irradiation was formed in a crescent shape or half-moon shape, and the width of the fusion-bonded section was wider in the central section in the thickness direction of the sheet laminate than both end sections (upper and lower end sections).

{Method for Evaluating Fusion-bonding Property}

The section that was cut and separated by the laser beam in the sheet laminate (fusion-bonded sheet article) after laser beam irradiation was observed with the eye. "O" indicates that the sheets' cut edge sections created by the cutting/separating were fusion-bonded, and "X" indicates that the cut edge sections were not fusion-bonded. More specifically, for each sheet laminate (fusion-bonded sheet article) after laser beam irradiation, the fusion-bonding property was evaluated on both sides, in the sheet laminate's transporting direction, of the section irradiated by the laser beam (the section overlapping the slit-shaped opening during laser beam irradiation); "O/O" indicates that both sides were fusion-bonded, "O/X" indicates that only one side (the side in a pressurized state during laser beam irradiation) was fusion-bonded, and "X/X" indicates that both sides were not fusion-bonded.

{Method for Evaluating Fusion-bond Strength}

The section that was cut and separated by the laser beam was cut out so as to have a width of 30 mm from each sheet laminate (fusion-bonded sheet article) after laser beam irradiation, and the cut-out section was employed as a measurement sample. The fusion-bond strength (seal strength) of each measurement sample was measured by using a tensile tester (Tensilon "RTC Series" from A&D Company, Limited). In the measurement, the two tab sections in the measurement sample that were not fusion-bonded and that were located on one-end side in the length direction of the measurement sample (the direction in which the sealed edge section extends) were pinched with the respective chucks of the tensile tester in such a manner that the measurement sample is peeled into two, each including half the number of sheets (two in the case of the sheet laminates 1 and 2, and one in the case of the sheet laminate 3) of the sheets constituting each measurement sample (four sheets in the sheet laminates 1 and 2, and two sheets in the sheet laminate 3), and the pinched tab sections were pulled in 180-degree opposite directions (T-peel test). The measurement was performed at a tensile speed (speed at which the chuck-to-chuck distance increases) of 300 mm/min, and the maximum strength was found. The measurement was performed n=20 times, and the average value of the maximum strength was considered the fusion-bond strength (unit: N/30 mm).

TABLE 1

|  | Examples | | | | | | Comp. Example | Ref. Example |
|---|---|---|---|---|---|---|---|---|
|  | 1 | 2 | 3 | 4 | 5*1 | 6 | 1*2 | 1 |
| Width W (mm) of slit-shaped opening (light passage section) [Distance W' (mm) from support member's end to spot's center] | 0.5 | 0.5 | 0.5 | 2.0 | [0.25] | 0.5 | — | 5.0 |
| Laser beam's spot diameter Φ (mm) | 0.20 | 1.00 | 3.50 | 0.20 | 0.20 | 0.20 | 0.20 | 0.20 |
| Φ/W [Φ/W'] | 0.4 | 2 | 7 | 0.1 | [0.8] | 0.4 | — | 0.04 |
| Sheet laminate 1  Fusion-bonding property | O/O | O/O | O/O | O/O | O/X | O/O | X/X | X/X |
| Fusion-bond strength (N/30 mm) | 16 | 21 | 28 | 10 | 16 | 15 | 0 | 0 |
| Sheet laminate 2  Fusion-bonding property | O/O | O/O | O/O | O/O | O/X | O/O | X/X | O/O |
| Fusion-bond strength (N/30 mm) | 22 | 26 | 31 | 17 | 22 | 22 | 0 | 9 |
| Sheet laminate 3  Fusion-bonding property | O/O | O/O | O/O | O/O | O/O | O/O | X/X | O/O |
| Fusion-bond strength (N/30 mm) | 11 | 18 | 30 | 6 | 11 | 13 | 0 | 4 |

*1Laser beam emitted onto belt-shaped sheet laminate in one-side pressurized state.
*2Laser beam emitted onto belt-shaped sheet laminate in non-pressurized state.

As shown in Table 1, in the sheet laminate after laser beam irradiation obtained in Comparative Example 1, the sheets' cut edge sections created by the cutting/separation by the laser beam irradiation were not fusion-bonded. In contrast, in the fusion-bonded sheet articles obtained in the Examples, the sheets' cut edge sections were fusion-bonded together and a fusion-bonded section (sealed edge section) was formed, and each fusion-bonded section had sufficient fusion-bond strength for practical use. Further, in Reference Example 1, no fusion-bonded section was formed when the sheet laminate 1 was used. It is surmised that the reason behind this is because the ratio (Φ/W) of the diameter Φ of the laser beam's spot on the sheet laminate with respect to the width W of the slit-shaped opening through which the laser beam is irradiated is less than 0.05 and the ratio Φ/W is smaller than that in the Examples, and thus, the sheets' cut edge sections created by the cutting/separation by the laser beam irradiation were not in a pressurized state in the thickness direction before the cutting/separation. From this, it can be understood that it is preferable to set the ratio Φ/W to 0.1 or greater in order to reliably obtain a fusion-bonded sheet article having sufficient fusion-bond strength for practical use.

Figure 13:
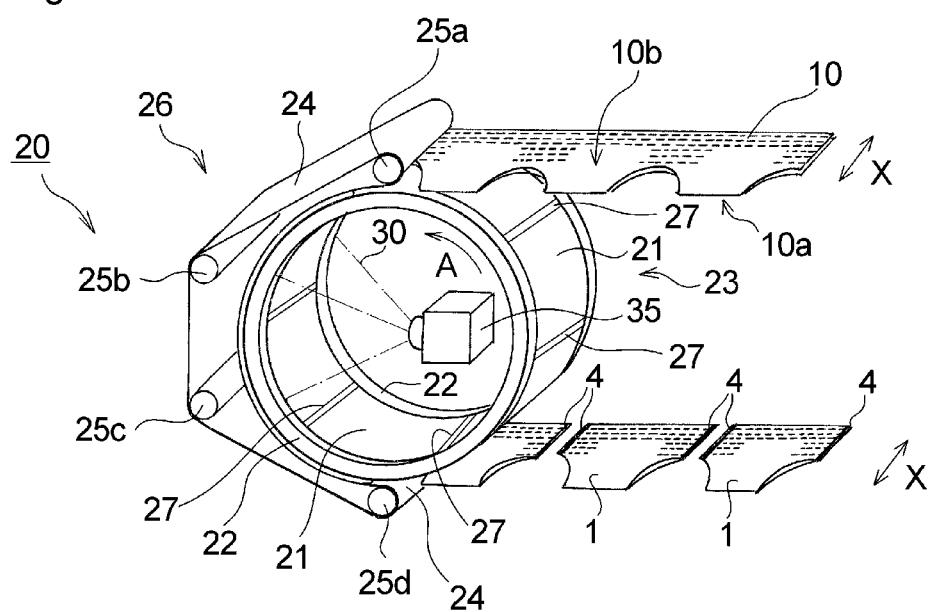
FIG. 13 is a schematic perspective view of an example of a method for manufacturing pull-on disposable diapers by using a laser joining device, which is an embodiment of an absorbent article manufacturing method of the present invention (second invention).

Below, a fusion-bonded sheet article manufacturing method according to the present invention (second invention) will be described—together with an absorbent article manufacturing method involving a fusion-bonded sheet article manufacturing step according to the present manufacturing method—in accordance with preferred embodiments with reference to the drawings. The explanation on the aforementioned first invention applies as appropriate to constituent features that are not particularly explained. FIG. 13 schematically illustrates a method for manufacturing pull-on disposable diapers (also referred to hereinafter simply as "diapers") by using a laser joining device, which is an embodiment of an absorbent article manufacturing method of the present embodiment. The fusion-bonded sheet article manufacturing method of the present invention involves a step of manufacturing a "fusion-bonded sheet article having sealed edge sections made by irradiating, with a laser beam, a belt-shaped sheet laminate in which a plurality of sheets are laminated and cutting and separating the sheet laminate, and fusion-bonding cut edge sections created, by the cutting/separation, in the plurality of sheets". In the diaper manufacturing method of the present embodiment illustrated in FIG. 13, a pull-on disposable diaper 1 including an outer cover 3 having a pair of side seal sections 4, 4, as illustrated in FIGS. 2 and 3, is manufactured as the fusion-bonded sheet article. Note that the outer cover 3 and the diaper 1 including the outer cover are both fusion-bonded sheet articles. It should be noted that, as regards the fusion-bonded sheet article, the "belt-shaped sheet laminate in which a plurality of sheets are laminated" literally encompasses a "form in which a plurality of sheets are laminated", and also "encompasses a "form in which a single sheet is folded so as to overlap".

The diaper 1 in the second invention is the same as the diaper 1 in the aforementioned first invention, and, as illustrated in FIGS. 2 and 3, the diaper 1 is a pull-on disposable diaper including an absorbent assembly 2, and an outer cover 3 that is arranged on a skin-non-contacting surface side of the absorbent assembly 2 and to which the absorbent assembly 2 is fixed, wherein a pair of side seal sections 4, 4, a waist opening 8, and a pair of leg openings 9, 9 are formed by joining both side edge sections of the outer cover 3 in a stomach-side section 1A and both side edge sections of the outer cover 3 in a back-side section 1B. The side seal sections 4 correspond to the aforementioned "sealed edge sections made by irradiating, with a laser beam, a belt-shaped sheet laminate in which a plurality of sheets are laminated and cutting and separating the sheet laminate, and fusion-bonding the cut edge sections created, by the cutting/separation, in the plurality of sheets".

In the diaper manufacturing method of the present embodiment, a continuous diaper strip 10 in which a plurality of sheet laminates (precursors of pull-on disposable diapers in which side seal sections have not yet been formed) are arranged continuously in one direction is manufactured separately as a "belt-shaped sheet laminate in which a plurality of sheets are laminated", and then, pull-on disposable diapers 1 (fusion-bonded sheet articles) each including an outer cover 3 (fusion-bonded sheet article) having a pair of side seal sections 4, 4 (sealed edge sections) are manufactured continuously by irradiating the continuous diaper strip 10 with a laser beam 30 as illustrated in FIG. 13, and thus, cutting and separating the continuous diaper strip into separate pieces, and, simultaneously, fusion-bonding the cut edge sections created, by the cutting/separation, in the plurality of sheets which are in a pressurized state.

The method for manufacturing the continuous diaper strip 10 (belt-shaped sheet laminate) in the second invention is the same as the method for manufacturing the continuous diaper strip 10 (belt-shaped sheet laminate) in the aforementioned first invention (cf. FIG. 4). It should be noted that no hot-melt adhesive needs to be applied to the waist section elastic members 5 and the hip section elastic members 6, and the elastic members may be fixed to the belt-shaped outer layer sheet 31 and the belt-shaped inner layer sheet 32 by a hot-melt adhesive applied to the sheet 31 or sheet 32.

In the present embodiment, as illustrated in FIG. 13, the continuous diaper strip 10 (belt-shaped sheet laminate), which has been manufactured separately as illustrated in FIG. 4, is irradiated with a laser beam by using a laser joining device 20, and thus, pull-on disposable diapers 1 (fusion-bonded sheet articles) each including an outer cover 3 (fusion-bonded sheet article) having a pair of side seal sections 4, 4 (sealed edge sections) are manufactured continuously.

The laser joining device 20 will be described. As illustrated in FIGS. 13 and 15, the laser joining device 20 is a fusion-bonded sheet article manufacturing device that continuously manufactures a plurality of fusion-bonded sheet articles (pull-on disposable diapers 1) each having sealed edge sections (side seal sections 4), by irradiating, with a laser beam 30, a belt-shaped sheet laminate (continuous diaper strip 10) in which a plurality of sheets are laminated and cutting and separating the continuous diaper strip, and fusion-bonding the cut edge sections created, by the cutting/separation, in the plurality of sheets. The laser joining device 20 includes: a support member 21 having an outer surface on which the continuous diaper strip 10 is arranged; an irradiation head 35 for emitting a laser beam 30; and a belt-type pressurizing means 26 as a pressurizing means. The support member 21 travels in a predetermined direction (the direction of arrow A in FIG. 13) in a state where the continuous diaper strip 10 is arranged on its outer surface, and has a light passage section (opening 27) through which the laser beam 30 can pass. The irradiation head 35 is arranged on the inner surface side of the support member 21, and emits the laser beam 30 toward the support member 21. The belt-type pressurizing means 26 pressurizes, from a side opposite from the support member 21, the continuous diaper strip 10 which is arranged on the outer surface of the support member 21.

More specifically, as illustrated in FIG. 13, the laser joining device 20 includes: a hollow cylindrical roller 23 provided with a hollow annular support member 21 that is driven to rotate in the direction of arrow A; an irradiation head 35 arranged in a hollow section of the support member 21 and emitting a laser beam 30; and, as a pressurizing means, a belt-type pressurizing means 26 provided with an endless pressurizing belt 24 (pressing member) and a plurality of (four) rollers 25a, 25b, 25c, 25d that rotate in a state where the pressurizing belt 24 is looped over the rollers. The laser joining device 20 also includes a tension adjustment mechanism (not illustrated) that can increase/decrease and adjust the tension on the pressurizing belt 24 to be wrapped around the outer peripheral surface of the annular support member 21 (the peripheral surface section of the cylindrical roller 23). By adjusting the tension, the pressure applied to the continuous diaper strip 10 (sheet laminate) by the support member 21 and the pressurizing belt 24 can be adjusted as appropriate.

The support member 21 forms the peripheral surface section (the section that abuts against the workpiece) of the cylindrical roller 23, and is sandwiched and fixed between a pair of annular frame bodies 22, 22 forming the respective left-and-right side edge sections of the cylindrical roller 23. In the present embodiment, the support member 21 is made of a single annular member, and is made of a metal material, such as iron, aluminum, stainless steel, or copper, or a heat-resistant material, such as a ceramic. It should be noted that the material for forming the annular frame bodies 22 may be selected from the same materials as the support member 21.

The annular support member 21 has a size that allows the continuous diaper strip 10 (belt-shaped sheet laminate)—which includes a plurality of diapers 1 (fusion-bonded sheet articles)—to be wrapped around the support member. The laser joining device 20 used in the present embodiment is, for example, a six-piece manufacturing device in which the number of manufactured diapers 1 (products) is set to six. The outer peripheral length of the cylindrical support member 21 constituting the device 20 is substantially the same as the length, in the length direction (transporting direction), of the continuous diaper strip 10 including six diapers 1. Thus, a region, in the outer peripheral surface of the annular support member 21, that is equivalent to approximately 60 degrees (=360 degrees/6 pieces) in terms of central angle of the support member 21 corresponds to a single diaper 1.

Here, the "outer peripheral length of the support member 21" refers to the entire length (perimeter) of the circumference of a circle (smallest circle) which is the smallest among circles that can contain the entire support member 21, when the annular support member 21 (cylindrical roller 23) is viewed in the direction of its rotation axis (central axis) as illustrated in FIG. 15 (in a side view of the support member 21). So, the respective lengths (PH, PL, PC), along the travel direction (circumferential direction), of later-described sections of the support member 21 (anterior holding region S1, holding region S2, and posterior holding region S3) are lengths of portions of the circumference of the smallest circle. More specifically, for example, if the support member 21 is cylindrical without projections and recesses on its outer peripheral surface—i.e., if the side-view contour of the support member 21 is a perfect circle—then the smallest circle coincides with the perfect circle, and so the outer peripheral length of the cylindrical support member 21 matches the perimeter of the perfect circle. On the other hand, for example, if the side-view contour of the support member 21 is polygonal, then the smallest circle coincides with a virtual perfect circle formed by connecting the vertices of the polygon, and so the outer peripheral length of this support member 21, which is polygonal in its side view, matches the perimeter of the virtual perfect circle. As described further below, a plurality of recesses 28 each capable of accommodating a portion of the sheet laminate (continuous diaper strip 10) (a portion thicker than other portions of the continuous diaper strip 10) may be formed in the outer surface of the support member 21 at predetermined intervals in the circumferential direction of the support member 21 (cf. FIG. 14). In such cases, the side-view contour of the support member 21 may macroscopically look like a perfect circle, but, microscopically (strictly speaking), cannot be considered a perfect circle, and may be polygonal. It should be noted that "annular" in the expression "annular support member 21" includes cases where the side-view contour has a perfectly circular cylindrical shape, and also cases where the contour has a shape other than a perfect circle, such as trapezoidal, triangular, or regular polygonal.

The support member 21 has light passage sections through which the laser beam can pass. As illustrated in FIGS. 13 and 14, the support member 21 of the present embodiment has, as the light passage sections, slit-shaped openings 27 that penetrate the support member 21 in the thickness direction. It should be noted that, in FIG. 14 (FIG. 14(*b*)), it is described as if the support member 21, the pressurizing belt 24 (pressing member), and the continuous diaper strip 10 (sheet laminate) sandwiched therebetween are moving horizontally from the left side toward the right side in FIG. 14 for the sake of brevity of explanation; in reality, however, these members move so as to rotate in a curved state corresponding to the cylindrical (annular) shape of the cylindrical roller 23. Each opening 27 is rectangular in a planar view, and its length direction matches the width direction of the support member 21 (the direction indicated by the reference sign X in FIG. 14(*a*); the direction parallel to the rotation axis of the cylindrical roller 23), and a plurality of the openings 27 are formed with predetermined intervals therebetween in the circumferential direction of the annular support member 21. As described above, the annular support member 21 in the present embodiment has a size that allows a continuous diaper strip 10 including six diapers 1 to be wrapped therearound, and so, there are six openings 27 to be used for cutting and separating the continuous diaper strip 10 into separate pieces. The support member 21 allows the laser beam to pass through at the openings 27, but does not allow the passage (transmission) of the laser beam at sections other than the openings 27. Methods for forming openings 27 in the support member 21 include: (1) a method of piercing the openings 27 by performing, for example, etching, punching, or laser processing, at predetermined sections in the support member 21; or (2) a method of using a plurality of curved rectangular members as the support member 21 instead of the single annular member, and arranging these members between the pair of frame bodies 22, 22 while leaving predetermined gaps therebetween in the circumferential direction of the frame bodies 22. In the method (2), the gap between two adjacent members becomes the slit-shaped opening 27.

As illustrated in FIG. 14(*b*), the support member 21 has, in its outer surface (the surface abutting against the workpiece), recesses 28 each capable of accommodating a portion of the workpiece (sheet laminate) (a portion thicker than other portions of the workpiece). A plurality of the recesses 28 are formed at predetermined intervals in the travel direction (circumferential direction) of the annular support member 21, and each slit-shaped opening 27 is formed in a region (i.e., protruding section) located between two adjacent recesses 28, 28. Each opening 27 is formed in the center of the protruding section in the travel direction (circumferential direction) of the annular support member 21. Each protruding section on the support member 21 (i.e., the region located between two adjacent recesses 28, 28) is a support region that directly receives the pressure from the workpiece (sheet laminate) wrapped around the outer surface of the support member 21 and that substantially supports the workpiece. In FIG. 14, the reference sign Wc indicates the length of a single protruding section (support region) along the travel direction (circumferential direction).

By forming the recesses 28 in the outer surface of the support member 21, it is possible to introduce the continuous diaper strip 10 on the outer surface of the support member 21 in a such manner that, if the thickness of the continuous diaper strip 10 (belt-shaped sheet laminate) is not uniform, the relatively thick parts in the continuous diaper strip 10 (e.g., the regions where the absorbent assemblies 2 are arranged) are accommodated in the recesses 28. By introducing the continuous diaper strip 10 onto the support member 21 in this way, the surface (the "other surface 10*b*") of the continuous diaper strip 10 abutting against the pressurizing belt 24 (pressing member) becomes substantially flat as illustrated in FIG. 14(*b*), and thus, when the pressurizing belt 24 is pressed against the continuous diaper strip 10, the entire section, in the continuous diaper strip 10, located on each protruding section (support region) where each opening 27 is formed (i.e., the section-to-be-cut/separated 10C and the vicinity thereof as illustrated in FIG. 14) is pressurized uniformly in the thickness direction by the pressurizing belt 24 and by the wrapping of the continuous diaper strip 10 onto the support member 21 by a predetermined tension. Thus, when this section, which is pressurized in the thickness direction before being cut/separated by laser beam irradiation, is irradiated with a laser beam and is cut and separated, the cut edge sections of the plurality of sheets constituting the cut/separated section can be fusion-bonded more reliably, and the fusion-bond strength of the side seal sections 4 (sealed edge sections) can be further improved.

In the present embodiment, the thickness of the continuous diaper strip 10 (belt-shaped sheet laminate) is partially different, and, in the later-described irradiation step, a section in the continuous diaper strip 10 having a relatively small thickness (i.e., a region where the absorbent assembly 2 is not arranged) is irradiated with the laser beam via the opening 27.

The belt-type pressurizing means 26 includes: the endless pressurizing belt 24 (pressing member); and four rollers 25a, 25b, 25c, 25d that rotate in a state where the pressurizing belt 24 is looped over them. The rollers 25a, 25b, 25c, 25d may be drive rollers, or may be driven rollers that follow the rotation of the cylindrical roller 23. As one or more of the rollers 25a, 25b, 25c, 25d and/or the cylindrical roller 23 is/are driven to rotate, the pressurizing belt 24 moves at the same speed as the cylindrical roller 23 (support member 21). It is preferable that the temperature of the support member 21 and the pressurizing belt 24 is maintained within a predetermined temperature range by air cooling, water cooling, or the like.

As for the pressurizing belt 24 (pressing member), it is possible to use a metal- or resin-made belt having heat resistance that can endure the heat generated during processing. The pressurizing belt 24 of the present embodiment is made of a metal material, such as iron, aluminum, or stainless steel. Further, in general, a belt that is not transmissive to the laser beam emitted onto the workpiece (continuous diaper strip 10) is used as the pressurizing belt 24, but a belt having such transmissivity may be used instead.

As illustrated in FIG. 13, in the hollow section of the hollow cylindrical roller 23 (support member 21) is provided an irradiation head 35 that emits a laser beam 30 toward the support member 21 forming the peripheral surface section of the cylindrical roller 23. The irradiation head 35 is a galvanoscanner (device with a mirror on the motor shaft) that can make the laser beam 30 scan freely, and includes, for example: a mechanism that makes the laser beam 30 move to and fro in a direction parallel to the rotation axis of the cylindrical roller 23 (i.e., the direction indicated by the reference sign X in FIG. 14(a)); a mechanism for moving, in the circumferential direction of the cylindrical roller 23, the position (irradiation point) where the laser beam 30 is incident on the continuous diaper strip 10 on the support member 21; and a mechanism for keeping the spot diameter of the laser beam 30 constant on the peripheral surface of the cylindrical roller 23. The irradiation head 35 does not have the function (light source) for generating the laser beam 30; the laser beam 30 is generated by a light source (not illustrated) arranged outside the cylindrical roller 23, and reaches the irradiation head 35 via an optical path (not illustrated) that links the light source and the irradiation head 35. With this configuration, the laser irradiation mechanism can move the irradiation point of the laser beam 30 discretionarily in both the circumferential direction of the cylindrical roller 23 and a direction orthogonal to the circumferential direction (i.e., the direction indicated by the reference sign X in FIG. 14(a); the direction parallel to the rotation axis of the cylindrical roller 23).

As illustrated in FIG. 13, the continuous diaper strip 10 (belt-shaped sheet laminate) is introduced onto the outer peripheral surface of the support member 21, which forms the peripheral surface section of the cylindrical roller 23 driven to rotate in the direction of arrow A, in a state where a predetermined tension is applied thereto by guide rollers, etc. (not illustrated). The continuous diaper strip 10 is then transported by a predetermined distance by the rotation of the cylindrical roller 23 in the circumferential direction thereof in a manner so as to be wrapped around the support member 21. Thereafter, the continuous diaper strip 10 is separated from the support member 21 by discharge rollers and nip rollers (not illustrated). By transporting the continuous diaper strip 10 in a manner so as to be wrapped around the support member 21, which forms the peripheral surface section of the cylindrical roller 23, with a predetermined tension applied thereto and so as to be pressurized by the pressurizing belt 24, sections of the continuous diaper strip 10 that are sandwiched between the support member 21 and the pressurizing belt 24, as well as the vicinity of those sections, are brought into a state where they are pressurized (compressed) in the thickness direction over a given continuous period of time from before being cut and separated by laser beam irradiation until a predetermined time passes after the cutting/separation. Thus, in cases where, for example, the continuous diaper strip 10 includes a nonwoven fabric, the continuous diaper strip 10 can be compressed more efficiently, and as a result, when the continuous diaper strip 10 in its compressed state is irradiated with a laser beam and is cut and separated, the cut edge sections of the plurality of sheets that constitute the cut/separated section can be fusion-bonded more reliably, thus further increasing the fusion-bonding strength of the side seal sections 4 (sealed edge sections).

The angle of rotation of the annular support member 21 (cylindrical roller 23) from when the continuous diaper strip 10 (belt-shaped sheet laminate) is introduced onto the support member 21 until it separates therefrom—i.e., the angle by which the continuous diaper strip 10 is wrapped around the support member 21—may be, for example, from 90 degrees to 270 degrees inclusive, and preferably from 120 degrees to 270 degrees inclusive. In the present embodiment, the angle by which the continuous diaper strip 10 is wrapped is approximately 180 degrees, and the length by which the continuous diaper strip 10 is wrapped amounts to approximately three diapers 1 (fusion-bonded sheet articles).

Further, the angular range (range of press-contact angle) for pressing the continuous diaper strip 10 into contact with the support member 21 by the pressurizing belt 24 (pressing member)—i.e., the angular range by which the pressurizing belt 24 is wrapped around the support member 21—is preferably from 90 to 270 degrees inclusive and more preferably from 120 to 270 degrees inclusive, if a case where the continuous diaper strip 10 is pressed in contact with the annular support member 21 (cylindrical roller 23) over the entire perimeter in its circumferential direction is considered as 360 degrees. In the diaper manufacturing method of the present embodiment, the continuous diaper strip 10 is pressurized in the thickness direction over a given continuous period of time from before the continuous diaper strip 10 is cut and separated by laser beam irradiation until a predetermined time passes after the cutting/separation; so, to make it possible to achieve this pressurized state of the continuous diaper strip 10, the angular range by which the pressurizing belt 24 is wrapped around the support member 21 (the press-contact angle) is set so as to be substantially the same as the angle by which the continuous diaper strip 10 is wrapped around the support member 21.

The fusion-bonded sheet article manufacturing method of the present embodiment is a method for manufacturing pull-on disposable diapers 1 by using the laser joining device 20 structured as above, and as illustrated in FIG. 13, while the continuous diaper strip 10 (belt-shaped sheet laminate) is continuously transported, one surface 10*a* thereof is made to abut against the outer surface of the support member 21 (outer peripheral surface of the annular support member 21), to bring the continuous diaper strip 10 into a pressurized state. As described above, the support member 21 forms the peripheral surface section of the cylindrical roller 23, and has slit-shaped openings 27 (light passage sections) through which the laser beam 30 can pass. By irradiating the continuous diaper strip 10, which is in a pressurized state, with the laser beam 30 from the support member 21 side via the opening 27, the continuous diaper strip 10 is cut and separated and, simultaneously, the cut edge sections, which have been created by the cutting and separation, in the plurality of sheets in the aforementioned pressurized state are fusion-bonded together. Thus, side seal sections 4 (sealed edge sections) are formed.

More specifically, as illustrated in FIG. 13, the pressurizing belt 24 (pressing member) is pressed against the other surface 10*b* of the continuous diaper strip 10 which is in abutment with the support member 21 (i.e., the surface on the opposite side from the one surface 10*a* which is the surface abutting against the support member 21), and the continuous diaper strip 10 in the aforementioned state is irradiated with a laser beam 30 from the support member 21 side via the slit-shaped opening 27, to thus continuously manufacture diapers 1 (fusion-bonded sheet articles) each including an outer cover 3 (fusion-bonded sheet article) having a pair of side seal sections 4, 4 (sealed edge sections). By irradiating the continuous diaper strip 10 with the laser beam 30 in a state where the continuous diaper strip is in a pressurized state (compressed state) by being sandwiched between the support member 21 and the pressurizing belt 24, it is possible to reliably fusion-bond the cut edge sections created in the plurality of sheets by the irradiation, and improve the fusion-bond strength of the side seal sections 4.

Figure 16:
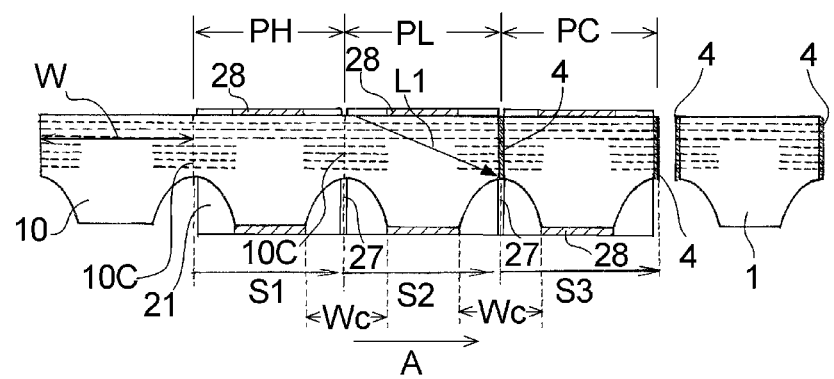
FIG. 16 is a diagram explaining the various steps in the manufacturing method illustrated in FIG. 13.

The fusion-bonded sheet article manufacturing method of the present embodiment will be described in further detail. As illustrated in FIGS. 13, 15, and 16, the fusion-bonded sheet article manufacturing method of the present embodiment involves: (i) an anterior holding step of arranging the continuous diaper strip 10 (belt-shaped sheet laminate) on the outer surface (outer peripheral surface) of the support member 21, which travels in a predetermined direction (direction of arrow A in FIG. 13) and which has an opening 27 (light passage section) through which the laser beam 30 can pass, and holding the continuous diaper strip 10 in a pressurized state on the support member's outer surface; (ii) an irradiation step of irradiating the continuous diaper strip 10, which is held in the pressurized state on the outer surface of the support member 21, with the laser beam 30, which has a wavelength that is absorbed by the sheets constituting the continuous diaper strip 10 and causes the sheets to generate heat, from the inner surface (inner peripheral surface) side of the support member 21 via the opening 27, and thus cutting and separating the continuous diaper strip 10; and (iii) a posterior holding step of, after termination of irradiation of the laser beam 30, holding the cut/separated continuous diaper strip 10 on the outer surface of the support member 21 while maintaining the pressurized state. In each step, "holding the belt-shaped sheet laminate (continuous diaper strip 10) on the outer surface of the support member 21" means that it will suffice if the sheet laminate is kept in a state where it substantially does not separate from the outer surface of the support member 21, and, for example, even if there are sections in the sheet laminate that are partially separated from the outer surface of the support member 21 due, e.g., to the contraction of the elastic members arranged in the sheet laminate, it is considered that the sheet laminate is held on the outer surface of the support member 21 if the sheet laminate, as a whole, is arranged along the outer surface of the support member 21. Further, as regards "maintaining the pressurized state" in the posterior holding step, although there are cases where the sheet laminate contracts somewhat in the posterior holding step due, e.g., to the cutting/separation in the previous irradiation step and/or the elastic members arranged in the sheet laminate, it is considered that the sheet laminate—even if it is in such a contracted state—is maintained in the pressurized state, so long as the sheet laminate is in a pressurized state within the bounds of not hindering the fusion-bonding of the sheets' cut edge sections.

In the anterior holding step of the present embodiment, the continuous diaper strip 10 (belt-shaped sheet laminate) is wound around the outer peripheral surface (outer surface) of the annular support member 21 that rotates about its central axis and that has openings 27 (light passage sections), and the continuous diaper strip is held in a pressurized state on the outer peripheral surface. It should be noted that the arrow indicated by the reference sign L1 in FIG. 16 represents the path taken by the laser beam 30 when the laser beam 30 is emitted, via the opening 27, onto the continuous diaper strip 10 on the support member 21 which travels in the direction of arrow A. After the termination of irradiation of the laser beam 30, the angle of the irradiation head 35 is adjusted as appropriate such that the laser beam 30 can again be emitted onto a predetermined irradiation start position (the base end of the arrow indicated by the reference sign L1).

The pressurized state of the continuous diaper strip 10 (sheet laminate) in each of the steps (the anterior holding step, irradiation step, and posterior holding step) is achieved by using the belt-type pressurizing means 26 and by pressing the pressurizing belt 24 (pressing member) against the surface 10*b* of the continuous diaper strip 10 on the opposite side from its surface 10*a* abutting against the support member 21.

It is desirable that the aforementioned pressurized state is achieved by a pressurizing force that keeps the continuous diaper strip 10 (sheet laminate), which is the workpiece, from moving during processing (i.e., during laser beam irradiation). From this viewpoint, the pressurizing force applied to the continuous diaper strip 10 (sheet laminate) in each of the steps (the anterior holding step, irradiation step, and posterior holding step)—and particularly in the anterior holding step and the irradiation step—is: preferably 50 kPa or greater, more preferably 100 kPa or greater; and preferably 160 kPa or less, more preferably 140 kPa or less; and more specifically, preferably from 50 kPa to 160 kPa inclusive, more preferably from 100 kPa to 140 kPa inclusive. The pressurizing force can also be adjusted by adjusting the pressing force by the pressurizing belt 24 (pressing member), and/or by adjusting the tension of the continuous diaper strip 10 on the support member 21.

The support member 21 includes regions corresponding to the aforementioned steps, and as illustrated in FIGS. 15 and 16, the support member 21 includes: an anterior holding region S1 corresponding to the anterior holding step and employed for holding the continuous diaper strip 10 (belt-shaped sheet laminate) before being irradiated with the laser beam 30; a holding region S2 corresponding to the irradiation step and employed for holding the continuous diaper strip 10 during the irradiation of the laser beam 30; and a posterior holding region S3 corresponding to the posterior holding step and employed for holding the continuous diaper strip 10 after being irradiated with the laser beam 30.

In the second invention, the way in which the continuous diaper strip 10 (belt-shaped sheet laminate) is cut and separated simultaneously with forming side seal sections 4 (sealed edge sections) by using the laser joining device 20 is the same as in the aforementioned first invention (cf. FIG. 6 or 7). That is, in the irradiation step, when the four-layer-structure section-to-be-cut/separated 10C is irradiated with the laser beam 30, the materials (fibers, etc.) forming the sheets 31, 32 in the section-to-be-cut/separated 10C generate heat due to direct exposure to the laser beam 30, and thus evaporate and disappear. Meanwhile, the aforementioned sheet-forming materials in the vicinity of the section-to-be-cut/separated 10C are indirectly heated by the laser beam 30 and melt. As a result, as illustrated in FIG. 6(c) or 7, the four-layer-structure section-to-be-cut/separated 10C is molten and cut, and thus, the continuous diaper strip 10 is cut and separated in such a manner that a single sheet laminate (diaper precursor; fusion-bonded sheet article) is isolated from the continuous diaper strip 10, and simultaneously, the cut edge sections created, by the cutting/separation, in the four sheets 31, 32 in the isolated sheet laminate, as well as the cut edge sections in the four sheets 31, 32 in the continuous diaper strip 10 from which the sheet laminate has been isolated, are fusion-bonded. These cut edge sections have been in a pressurized state (compressed state) by being sandwiched between the support member 21 and the pressurizing belt 24, even during the anterior holding step which is before their formation (i.e., before the continuous diaper strip 10 is cut and separated by being irradiated with the laser beam 30). According to the diaper manufacturing method of the present embodiment, the cutting/separation of the belt-shaped sheet laminate and the fusion-bonding of the sheets' cut edge sections, which have been created in two sites by the cutting/separation and which are in a pressurized state, are performed simultaneously by a single laser beam irradiation. Thus, compared to methods in which two fusion-bonded sites are formed by performing laser beam irradiation twice (i.e., methods outside the scope of the present invention), fusion-bonding and cutting/separation can be performed in a single step with substantially half the laser output, and thus, diapers 1 can be manufactured efficiently. Further, because fusion-bonding and cutting/separation can be performed in the same step, non-sealed edge sections—in which the sheets' cut edge sections are not fusion-bonded together—will not be created, and thus, this step is also effective in material reduction.

The cut edge sections of the sheets 31, 32 are in a molten state due to heat generation during, and immediately after the termination of, the irradiation with the laser beam 30 (immediately after the termination of the irradiation step). However, after the termination of irradiation, the cut edge sections are rapidly cooled by ambient air and solidify, because the cut/separated parts of the continuous diaper strip 10—i.e., the continuous diaper strip 10 and the single piece of sheet laminate (diaper precursor; fusion-bonded sheet article) isolated from the continuous diaper strip 10 by irradiation with the laser beam 30—are maintained in their pressurized state by the support member 21 and the pressurizing belt 24 in the subsequent posterior holding step. Thus, the cut edge sections are made into fusion-bonded sections 40 in which the materials (fibers, etc.) forming the cut edge sections are molten and integrated together. By the formation of the fusion-bonded section 40, one side seal section of the pair of side seal sections 4, 4 in a single diaper 1 is formed.

In the posterior holding step, if necessary, the continuous diaper strip 10 (the cut/separated sheet laminate) and the single piece of sheet laminate (diaper precursor) isolated from the continuous diaper strip 10 may be forcibly cooled—i.e., the cut edge sections of the sheets 31, 32 may be forcibly cooled, to thereby promote the formation of the fusion-bonded sections 40. Examples of cooling methods applicable to the forcible cooling include: (A) a method of providing a known circulation cooling structure to the support member 21 and/or the pressurizing belt 24 (pressing member); and (B) an air-cooling method of blowing an air stream onto the object to be cooled (the cut/separated sheet laminate).

After a single section-to-be-cut/separated 10C is cut and separated, the laser beam 30 is moved so that its irradiation point is incident on another opening 27 adjacent to the current opening in a direction opposite to the transporting direction A, and the laser beam 30 is emitted through this other opening 27 onto another section-to-be-cut/separated 10C which is positioned thereon. Thus, this other section-to-be-cut/separated 10C is cut/separated and fusion-bonded in the same manner, and the other side seal section 4 (fusion-bonded section 40) forming a pair with the previously-formed side seal section 4 is formed. The same operation is repeated thereafter, thus continuously manufacturing pull-on disposable diapers 1 (fusion-bonded sheet articles) each including an outer cover 3 (fusion-bonded sheet article) having a pair of side seal sections 4, 4 (sealed edge sections).

As described above, in the diaper (fusion-bonded sheet article) manufacturing method of the present embodiment, all of the aforementioned steps (the anterior holding step, irradiation step, and posterior holding step) are executed on a continuous diaper strip 10 (belt-shaped sheet laminate) that is wrapped around an annular support member 21 (cylindrical roller 23). By executing a plurality of steps on a workpiece (sheet laminate) which is wrapped around a single annular support member 21, it is possible to make the manufacturing device compact, and improve the positional accuracy in cutting/separating the sheet laminate with a laser beam.

From the viewpoint of making the manufacturing device compact and improving the positional accuracy in cutting/separating the sheet laminate, it is preferable that the relationship shown in the following Formula (1) holds true between the product width W and the dimensions of the manufacturing device. As illustrated in FIG. 16, the product width W is the width of a single fusion-bonded sheet article (diaper precursor; diaper 1)—i.e., the product width W is the length (unit: mm), in the transporting direction, of each of a plurality of fusion-bonded sheet articles included in the belt-shaped sheet laminate (continuous diaper strip 10), and is the length of the diaper 1 along the travel direction of the support member 21 (the diaper's length along the circumferential direction of the annular support member 21). Further, in Formula (1) below: L is the laser irradiation distance (unit: mm; cf. FIG. 15); and G is the dimension (unit: mm)

of the laser beam irradiation head 35 arranged on the inner surface side (in the hollow section) of the support member 21. The laser irradiation distance L is the distance from the laser beam radiating position on the outer surface of the irradiation head 35 (e.g., the section, on the outer surface of a protection glass of the irradiation head, where the laser beam passes) to the support member 21's outer peripheral surface (the surface abutting against the sheet laminate) which is the object irradiated by the laser beam.

[Math. 2]

$$\pi(L+G) \leq n \cdot W \quad (1)$$

This Formula (1) is obtained as follows. The relationship shown in the following Formula (1-a) holds true among: the product width W; the number "n" of products obtained by the support member 21 (number of products; six in the present embodiment); and the diameter D of the support member 21 (cf. FIG. 15).

Further, if it is assumed that the center of the lens of the laser beam irradiation head 35 arranged on the inner surface side (in the hollow section) of the support member 21 is at half the entire width of the irradiation head 35, then the dimension G (unit: mm) of the irradiation head 35 is expressed by the following Formula (1-b). In Formula (1-b), GH is the height of the irradiation head 35 (the length along the laser beam irradiation direction; unit: mm; cf. FIG. 15), and GW is the width of the irradiation head 35 (the length in the direction orthogonal to the laser beam irradiation direction; unit: mm; cf. FIG. 15). The dimension G is the diagonal dimension (maximum dimension) of the irradiation head 35.

Further, in order to fit the irradiation head 35 on the inner surface side (in the hollow section) of the annular support member 21 (cylindrical roller 23) while ensuring a predetermined laser irradiation distance L, the following Formula (1-c) must be satisfied.

Substituting Formula (1-a) into Formula (1-c) yields the aforementioned Formula (1).

[Math. 3]

$$\frac{n \cdot W}{\pi} = D \quad (1\text{-a})$$

$$G = \sqrt{(GH^2 + (GW/2)^2)} \quad (1\text{-b})$$

$$L + G \leq D \quad (1\text{-c})$$

Further, it is preferable that the length PL (cf. FIG. 16), along the circumferential direction (travel direction) of the support member 21, of a region in the support member 21 where the irradiation step is executed (i.e., the holding region S2) is shorter than the length, along the circumferential direction, of a single diaper 1 (fusion-bonded sheet article) (i.e., the product width W)—i.e., the relationship PL<W holds true. By satisfying this relationship, continuous manufacturing of fusion-bonded sheet articles with a single irradiation head is made efficient. Here, the length PL (unit: mm) of the holding region S2 is the length, along the circumferential direction, of a region on the outer peripheral surface of the annular support member 21 where the irradiation step is executed (i.e., the outer peripheral length of the region S2). On the premise that the relationship PL<W holds true, the length PL is: preferably 0.008 times or greater, more preferably 0.04 times or greater, the product width W; and preferably 0.9 times or less, more preferably 0.8 times or less, the product width W; and more specifically, preferably from 0.008 times to 0.9 times inclusive, more preferably from 0.04 times to 0.8 times inclusive, the product width W.

Further, it is preferable that the length PC (cf. FIG. 16), along the circumferential direction (travel direction) of the support member 21, of a region in the support member 21 where the posterior holding step is executed (i.e., the posterior holding region S3) is from 0.4 times to 12 times, inclusive, the length PL. The length PC is: preferably 0.4 times or greater, more preferably 1 time or greater, even more preferably 1.5 times or greater, the length PL; and preferably 12 times or less, more preferably 7.5 times or less, even more preferably 6 times or less, the length PL; and more specifically, preferably from 0.4 times to 12 times inclusive, more preferably from 1 time to 7.5 times inclusive, even more preferably from 1.5 times to 6 times inclusive, the length PL.

As described above, in the posterior holding step, the cut edge sections in the sheets 31, 32 created by laser beam irradiation are in their molten state and have flowability immediately after the termination of laser beam irradiation. By satisfying the aforementioned relationship between the length PL of the holding region S2 and the length PC of the posterior holding region S3, the cut edge sections of the sheets 31, 32 in their molten state can be cooled and solidified in the posterior holding region S3 while suppressing them from flowing, and as a result, a fusion-bonded sheet article (diaper 1) having sufficient fusion-bond strength for practical use can be obtained. If the length PC of the posterior holding region S3 is less than 0.4 times the length PL of the holding region S2, there is a possibility that sufficient fusion-bond strength for practical use cannot be achieved, whereas if the length PC is greater than 12 times the length PL, the support member 21 may become too large, which may increase the size of the manufacturing device (laser joining device 20).

The aforementioned preferable relationship "the length PC of the posterior holding region S3 is from 0.4 times to 12 times, inclusive, the length PL of the holding region S2" can be expressed by the following Formula (2). In Formula (2): W is the aforementioned product width; N is the processing speed (unit: pieces/min.), i.e., the number of fusion-bonded sheet articles (diapers 1) produced per unit time; and CS is the cooling time (unit: sec.), i.e., the time necessary for a section (cut edge sections in the sheets 31, 32) in a molten state (state exhibiting flowability) by the laser beam irradiation to be cooled and solidify (to lose flowability).

[Math. 4]

$$0.4 \cdot PL \leq PC \leq 12 \cdot PL \quad (2)$$

This Formula (2) is obtained as follows. The relationship shown in the following Formula (2-a) holds true among: the length PL of the holding region S2; the transporting speed v (unit: m/min.; cf. FIG. 15) of the sheet laminate (continuous diaper strip 10) on the support member 21; and the laser beam irradiation time LS (unit: sec.).

The transporting speed v is expressed as in the following Formula (2-b) by using the processing speed N and the product width W.

The laser beam irradiation time LS is expressed by the following Formula (2-c), by substituting Formula (2-b) into Formula (2-a).

The relationship shown in the following Formula (2-d) holds true among: the length PC of the posterior holding region S3; the transporting speed v (unit: m/min.; cf. FIG.

15) of the sheet laminate (continuous diaper strip 10) on the support member 21; and the cooling time CS (unit: sec.).

The cooling time CS is expressed by the following Formula (2-e), by substituting Formula (2-b) into Formula (2-d).

According to the Inventors' finding, in manufacturing pull-on disposable diapers 1 of the type illustrated in FIG. 2, the fusion-bond strength of the side seal section 4 (sealed edge section) becomes stable at a sufficient level for practical use if more than or equal to 0.2 seconds of cooling time CS can be ensured. Further, considering the range of products to which the manufacturing method of the present invention is applicable, the aforementioned "more than or equal to 0.2 seconds of cooling time CS" corresponds to a range from 0.4 times to 12 times the laser beam irradiation time LS. Thus, the relationship shown in the following Formula (2-f) holds true between the cooling time CS and the laser beam irradiation time LS.

The aforementioned Formula (2) is obtained by substituting Formulae (2-c) and (2-e) into Formula (2-f) and rearranging the formula.

[Math. 5]

$$\frac{PL}{1000 \cdot v} = LS \quad (2\text{-a})$$

$$v = \frac{N \cdot W}{60 \cdot 1000} \quad (2\text{-b})$$

$$LS = \frac{PL \cdot 60}{N \cdot W} \quad (2\text{-c})$$

$$\frac{PC}{1000 \cdot v} = LS \quad (2\text{-d})$$

$$CS = \frac{PC \cdot 60}{N \cdot W} \quad (2\text{-e})$$

$$0.4 \cdot LS \leq CS \leq 4 \cdot LS \quad (2\text{-f})$$

Further, it is preferable that the length PH (cf. FIG. 16), along the circumferential direction (travel direction) of the support member 21, of a region in the support member 21 where the anterior holding step is executed (i.e., the anterior holding region S1) is longer than the length, along the circumferential direction, of a single diaper 1 (fusion-bonded sheet article) (i.e., the product width W)—i.e., the relationship PH>W holds true. By satisfying this relationship, the anterior holding region S1 will bear one or more fusion-bonded sheet articles (diapers 1) in a form where they are included in the sheet laminate (continuous diaper strip 10), and thus, it is possible to effectively prevent the disadvantage that the sheet laminate cannot be transported because the holding of the sheet laminate is released by cutting/separating the sheet laminate by laser beam irradiation.

It should be noted that, as regards the length PH in the support member 21, in cases where a plurality of recesses 28 are formed in the outer surface of the support member 21 at predetermined intervals in the circumferential direction (travel direction) of the support member 21 as illustrated in FIG. 14, the aforementioned relationship PH>W does not necessarily have to hold true, and instead, it is preferable that the relationship PH>Wc described below holds true, from the viewpoint of achieving the aforementioned effect (the effect obtained by the satisfaction of the relationship PH>W). That is, it is preferable that the length PH (cf. FIG. 16), along the circumferential direction (travel direction) of the support member 21, which has a plurality of recesses 28 formed in its outer surface, is longer than the length Wc (cf. FIGS. 14 and 16), along the circumferential direction (travel direction), between two adjacent recesses 28, 28 (i.e., each protruding section (support region)) in the support member 21—i.e., the relationship PH>Wc holds true. By satisfying this relationship, the aforementioned effect is achieved, because the anterior holding region Si will include one support region in a form included in the sheet laminate (continuous diaper strip 10), and thus, the continuous diaper strip 10 is held by the support region before the irradiation step, without fail. From the viewpoint of achieving the aforementioned effect more reliably, it is more preferable that the length PH of the anterior holding region S1 in the support member 21, which has a plurality of recesses 28 formed in its outer surface, is equal to or longer than the product width W of at least one diaper 1.

Further, from the viewpoint of making the manufacturing device compact and improving the positional accuracy in cutting/separating the sheet laminate, it is preferable that the region necessary for executing all of the aforementioned steps (the anterior holding step, irradiation step, and posterior holding step) is within 360 degrees in terms of central angle of the annular support member 21 (cylindrical roller 23)—i.e., it is preferable that the following Formula (3) holds true. The reference signs in Formula (3) are as described above.

[Math. 6]

$$PH + PL + PC \leq n \cdot W \quad (3)$$

One main characteristic feature of the diaper 1 manufactured as above lies in the side seal sections 4. The side seal sections 4 (fusion-bonded sections 40) in the second invention are the same as those in the aforementioned first invention (cf. FIGS. 6(c), 7, and 8).

Incidentally, in the foregoing embodiment (cf. FIG. 13), the pressurized state of the continuous diaper strip 10 (sheet laminate) in each of the steps (anterior holding step, irradiation step, and posterior holding step) is achieved by using the belt-type pressurizing means 26, but the method for achieving the pressurized state of the sheet laminate in the present invention is not limited thereto, and for example, instead of the belt-type pressurizing means 26, the pressurized state can be achieved by "a pressurizing means including: a pressing plate (pressing member) provided so as to be capable of performing a reciprocating motion between the outer surface of the support member 21 and a predetermined standby position outside the support member's outer surface (i.e., outside the annular support member 21 in its radial direction); and a cam mechanism that transmits the rotation of the support member 21 about its central shaft (rotation axis) (i.e., the traveling, in the predetermined direction, of the support member) by converting the rotation (traveling) into reciprocating motion of the pressing plate (pressing member)". A specific example of a pressurizing means having such a cam mechanism is the processing device described in JP 2005-212149 A, and this processing device can be applied to the present invention as appropriate.

Figure 17:
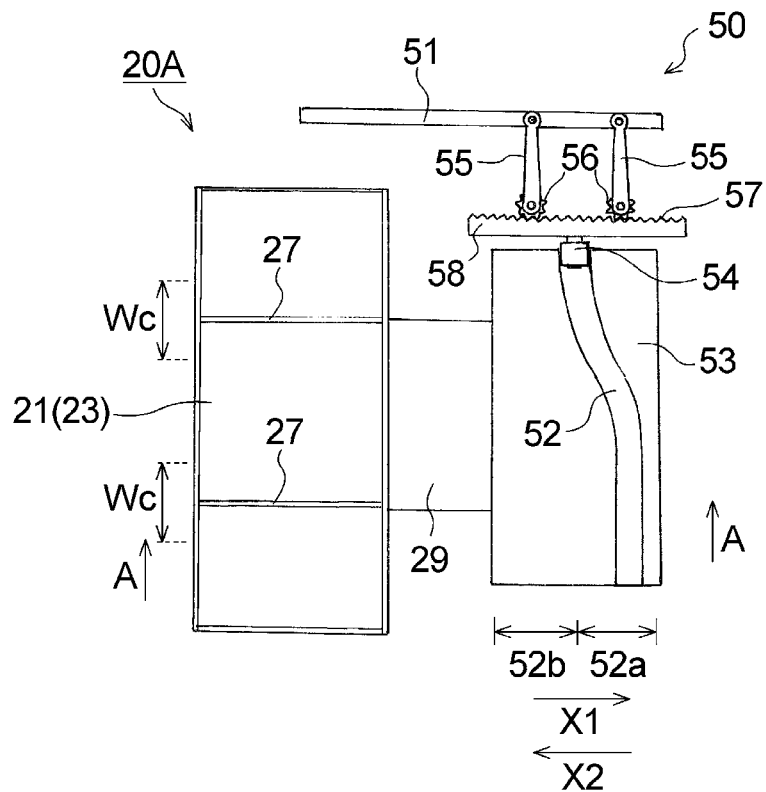
FIG. 17 is a diagram illustrating a modified example of the manufacturing device (laser joining device) illustrated in FIG. 13.

FIG. 17 illustrates a laser joining device 20A which is an example of a laser joining device (fusion-bonded sheet article manufacturing device) including a pressurizing means 50 with a cam mechanism. The following description regarding this laser joining device 20A mainly focuses on constituent parts that are different from those in the aforementioned laser joining device 20 including a belt-type pressurizing means 26, and similar constituent parts are accompanied by the same reference signs and explanation thereof is omitted. The explanation on the aforementioned laser joining device 20 applies as appropriate to constituent parts that are not particularly explained.

As illustrated in FIG. 17, the pressurizing means 50 included in this laser joining device 20A includes: a pressing plate 51 (pressing member) provided so as to be capable of performing a reciprocating motion between a predetermined standby position outside the outer surface (outer peripheral surface) of the annular support member 21 (cylindrical roller 23) and this outer peripheral surface; and a cam mechanism that transmits the rotation of the support member 21 about its central shaft 29 by converting this rotation into reciprocating motion of the pressing plate 51 (pressing member). More specifically, the pressurizing means 50 includes, in addition to the pressing plate 51 (pressing member): a cylindrical cam 53 (driver) that is arranged on the central shaft 29 of the support member 21 in parallel to the support member 21 and that has a cam groove 52 having a specific shape formed in its outer peripheral surface; and a rack 58 (follower) that has a cam follower 54 attached to its inner surface (the surface opposing the cylindrical cam 53) and that has rack teeth 57 formed on its outer surface. The cam follower 54 engages with the cam groove 52. The rack teeth 57 mesh with pinions 56 attached to respective links 55 on the pressing plate 51 (pressing member). The cylindrical cam 53 and the rack 58 are coupled by the engagement of the cam follower 54 of the rack 58 with the cam groove 52 of the cylindrical cam 53, thus constituting the aforementioned cam mechanism.

The cylindrical cam 53 is a cylindrical roller that rotates about the central shaft 29 in synchronization with the support member 21, and is supported so as to be rotatable in the same direction as the support member 21 by the same drive source (not illustrated) as the support member 21. As illustrated in FIG. 17, the cylindrical cam 53 has a smaller outer diameter than the annular support member 21 (cylindrical roller 23). The cam groove 52 formed in the outer peripheral surface of the cylindrical cam 53 is a single groove that is continuous over the entire length of the outer peripheral surface in the circumferential direction. The cam groove 52 has a section 52a farther from the support member 21 and a section 52b closer to the support member 21, with reference to a center line (not illustrated) that bisects the cylindrical cam's outer peripheral surface in a direction parallel to the central shaft 29.

The rack 58 is a plate-shaped member that is, as a whole, curved so as to protrude toward the opposite direction from the cylindrical cam 53 side, and the rack's inner surface and outer surface are both parallel to the outer peripheral surface of the cylindrical cam 53. The rack 58 is fixed at a predetermined position in the circumferential direction of the cylindrical cam 53, and the rack does not move in the circumferential direction even when the cylindrical cam 53 rotates. However, in the direction parallel to the central shaft 29 of the cylindrical cam 53 (support member 21) (i.e., the left-and-right direction in FIG. 17), the rack 58 moves in directions corresponding to the shape of the cam groove 52 (i.e., the direction indicated by reference sign X1 or X2 in FIG. 17) by the interaction between the cam groove 52 and the cam follower 54.

On the outer surface of the rack 58, a multitude of rack teeth 57 are formed so as to be aligned in a row in a direction parallel to the central shaft 29 of the cylindrical cam 53 (support member 21), and two pinions 56, 56 mesh with the rack teeth 57. Each of the two pinions 56, 56 is substantially disk-shaped in a planar view, and teeth are formed continuously on its outer peripheral surface, and the teeth of each pinion 56 mesh with the rack teeth 57 of the rack 58. The rotation shaft of each of the two pinions 56, 56 is fixed in the rotation axis direction of the cylindrical cam 53, and thus moves with respect to the rack 58 but does not move in the rotation axis direction of the cylindrical cam 53. When the rack 58 moves in the direction X1 (moves away from the support member 21), the two pinions 56, 56 rotate in a direction (direction X2) opposite from the direction X1 along the row of rack teeth 57 while meshing therewith; when the rack 58 moves in the direction X2 (moves closer to the support member 21), the two pinions 56 rotate in a direction (direction X1) opposite from the direction X2 along the row of rack teeth 57 while meshing therewith.

Figure 18A:
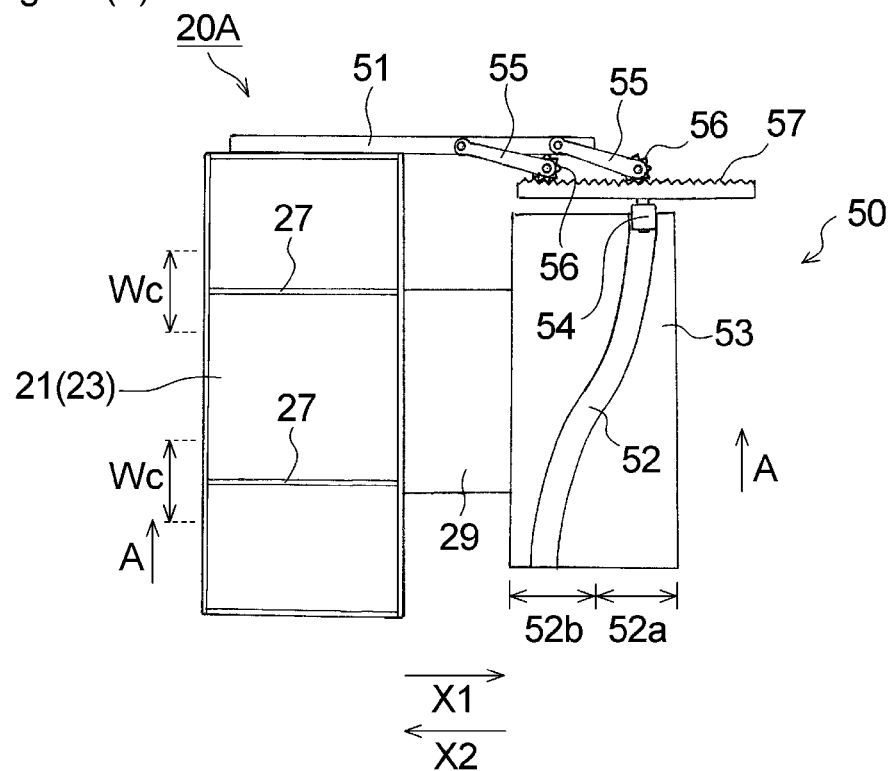
FIGS. 18(*a*) and 18(*b*) are diagrams explaining the operations of a pressurizing means illustrated in FIG. 17.

The pressing plate 51 (pressing member) is a plate-shaped member that is, as a whole, curved so as to protrude toward the opposite side from the cylindrical cam 53 side, and the pressing plate's inner surface and outer surface are both parallel to the outer peripheral surface of the cylindrical cam 53. The pressing plate 51 (pressing member) is coupled so as to be pivotable above the outer peripheral surface of the cylindrical cam 53 by the two links 55, 55 extending from the respective pinions 56, 56 on the outer surface of the rack 58. One end of each of the two links 55, 55 engages with the inner surface (surface opposing the rack 58) of the pressing plate 51 (pressing member), and the other end is fixed to the rotary center of each pinion 56. The pressing plate 51 (pressing member) is formed in such a manner that a portion thereof is abuttable against the outer peripheral surface of the support member 21 as described below (cf. FIG. 18(a)), and the section abutting against the outer peripheral surface of the support member 21 has a size that can cover the entirety of one opening 27, and its peripheral section, formed in the support member's outer peripheral surface—i.e., a size that can cover one protruding section (support region) on the support member 21. The length of this abutting section of the pressing plate 51 (pressing member) along the circumferential direction (travel direction) is equal to or longer than the length Wc of one protruding section along the circumferential direction.

Figure 18B:
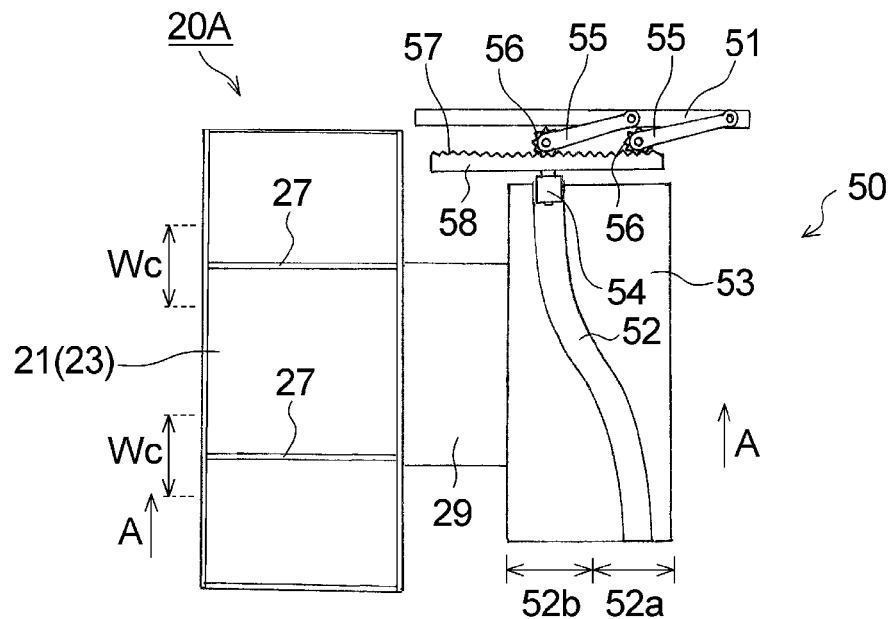
Figure 19:
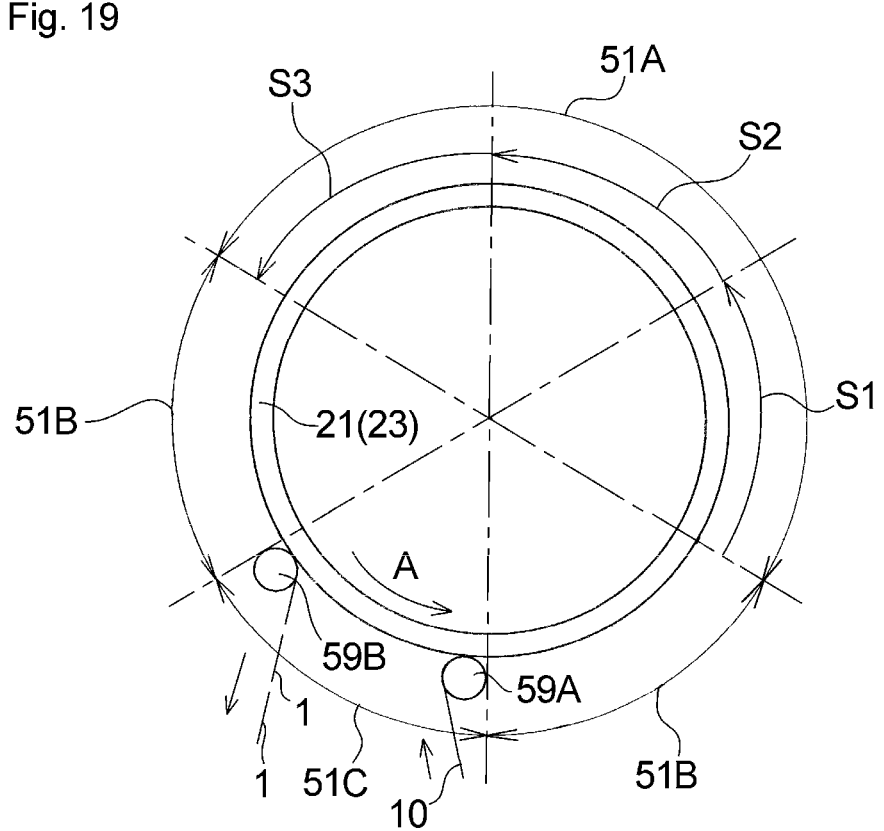
FIG. 19 is a diagram explaining the relationship between a support member and various states of a pressing plate (pressing member) in the pressurizing means illustrated in FIG. 18.

As illustrated in FIG. 17, when the two links 55, 55 are in their upright state (a state where the two links 55, 55 stand upright from their respective pinions 56 in parallel to the direction of the normal to the cylindrical cam 53), the pressing plate 51 (pressing member) is in a state where it is located in a predetermined standby position outside the outer peripheral surface of the support member 21 (cylindrical roller 23) (a form of a transition state illustrated by reference sign 51B in FIG. 19), and the earn follower 54 is in a state where it is located on the aforementioned center line (not illustrated) that bisects the cylindrical cam 53's outer peripheral surface in a direction parallel to the central shaft 29, or in the vicinity thereof (i.e., on the boundary between the section 52a and section 52b or in the vicinity thereof). When the support member 21 rotates in the direction A from the state illustrated in FIG. 17 and the cylindrical cam 53 also rotates in the direction A in synchronization therewith, the rack 58 (cam follower 54) moves in the direction X1—which is the direction following the shape of the cam groove 52's section 52a farther from the support member 21—and, in association with the rack 58's movement in the direction X1, the two pinions 56, 56 on the rack 58 rotationally move in the direction (direction X2) opposite from the direction X1. Due to the rotational movement of the pinions 56 in the direction X2, the links 55 fixed to the respective pinions 56 change from the upright state illustrated in FIG. 17 to a state where they collapse toward the support member 21 as illustrated in FIG. 18(*a*). At this time, a section of the pressing plate 51 (pressing member) on the side closer to the support member 21 abuts against a portion of the outer peripheral surface of the support member 21 and comes into a state where it pressurizes this portion of the support member (pressurized state illustrated by reference sign 51A in FIG. 19). So, if a sheet laminate is present on this portion of the support member, then the pressing plate 51 (pressing member) will be pressed against the sheet laminate's surface on the opposite side from its surface abutting against the support member 21, and, in this way, the pressurized state of the sheet laminate in each of the aforementioned steps (anterior holding step, irradiation step, and posterior holding step) is achieved.

Further, when the cylindrical cam 53 rotates in the direction A from the state where the two links 55, 55 are collapsed toward the support member 21 as illustrated in FIG. 18(*a*), the rack 58 (cam follower 54), which has been in a position farthest from the support member 21, moves in the direction X2—which is the direction following the shape of the cam groove 52 (sections 52*a* and 52*b*)—and, in association with the rack 58's movement in the direction X2, the two pinions 56, 56 on the rack 58 rotationally move in the direction (direction X1) opposite from the direction X2. Due to the rotational movement of the pinions 56 in the direction X1, the links 55 fixed to the respective pinions 56 change from the state where they are collapsed toward the support member 21, as illustrated in FIG. 18(*a*), to a state where they collapse toward the opposite side from the support member 21 side, as illustrated in FIG. 18(*b*), via the upright state illustrated in FIG. 17. Thus, the pressing plate 51 (pressing member), which has been abutting against the outer peripheral surface of the support member 21, separates from the outer peripheral surface, undergoes the predetermined standby position, and comes into a state where it is located at the farthest position from the support member 21 (farthest-position standby state indicated by reference sign 51C in FIG. 19). In this way, the sheet laminate's aforementioned pressurized state in each of the aforementioned steps (anterior holding step, irradiation step, and posterior holding step) is cancelled.

FIG. 19 illustrates the relationship between the support member 21 and the various states of the pressing plate 51 (pressing member)—i.e., the "state in which the pressing plate 51 (pressing member) pressurizes the outer peripheral surface of the support member 21" (pressurized state 51A), and the "state in which the pressing plate 51 (pressing member) is located at the farthest position from the support member 21" (farthest-position standby state 51C). The reference sign 51B in FIG. 19 indicates a state (transition state) in which the pressing plate 51 (pressing member) transitions from the farthest-position standby state 51C to the pressurized state 51A, or from the pressurized state 51A to the farthest-position standby state 51C. In the embodiment illustrated in FIG. 19, before the continuous diaper strip 10 (belt-shaped sheet laminate) is introduced onto the support member 21 (cylindrical roller 23) by being guided by a guide roller 59A, the pressing plate 51 (pressing member) transitions from the farthest-position standby state 51C (cf. FIG. 18(*b*)) to the pressurized state 51A (cf. FIG. 18(*a*)) via the transition state 51B illustrated in FIG. 17, and maintains the pressurized state 51A in the anterior holding region S1 corresponding to the anterior holding step, the holding region S2 corresponding to the irradiation step, and the posterior holding region S3 corresponding to the posterior holding step. Then, within a region downstream of the posterior holding region S3 in the rotating direction A (transporting direction) and upstream, in the rotating direction A (transporting direction), of a position where a diaper 1 (fusion-bonded sheet article) produced by the cutting/separation of the continuous diaper strip 10 is guided by a guide roller 59B and separated from the support member 21 (i.e., a section where the guide roller 59B and the support member 21 come the closest), the pressing plate 51 (pressing member) transitions from the pressurized state 51A to the farthest-position standby state 51C via the transition state 51B. The shape of the cam groove 52 of the pressurizing means 50 is set so as to cause the pressing plate 51 (pressing member) to transition between the aforementioned states as described above. It should be noted that the outer peripheral surface of the support member 21 has a multitude of fine suction holes (not illustrated) that generate a suction force that allows the workpiece (continuous diaper strip 10) to be sucked onto the outer peripheral surface, and when the pressing plate 51 (pressing member) is in the transition state 51B, the continuous diaper strip 10 is sucked and held onto the outer peripheral surface of the support member 21 by the suction force through the suction holes. A not-illustrated suction means (negative pressure source) is connected to the support member 21 (cylindrical roller 23), and by activating the suction means, the inside of the fine holes can be maintained at a negative pressure, and suction force is generated by the fine holes. For example, the suction mechanism described in JP 2007-260875 A may be employed as the suction mechanism for the support member 21.

The pressurizing means 50 includes at least one pressurizing mechanism which includes the pressing plate 51 (pressing member) and the constituent members (cam follower 54, links 55, pinions 56, rack 58, etc.) of the cam mechanism except for the cylindrical cam 53. For example, the pressurizing means 50 may be configured so as to include the same number of pressurizing mechanisms (six in the present embodiment) as the number of openings 27 (light passage sections) formed in the support member 21, in such a manner that each pressurizing mechanism (pressing plate 51 (pressing member)) is in one-to-one correspondence with each opening 27.

The laser beam employed in the present invention (second invention) is the same as the laser beam employed in the aforementioned first invention.

As with the fusion-bonded sheet article manufactured by the aforementioned first invention, the fusion-bonded sheet article manufactured by the present invention (second invention) may be used as-is, or may be integrated with other components and used as various articles.

The present invention (second invention) has been described above according to embodiments thereof, but the present invention is not limited to the foregoing embodiments and may be modified as appropriate within a scope that does not depart from the gist of the present invention. For example, the second invention may be modified in the same way as the modifications in the aforementioned first invention. Further, thread-shaped or band-shaped elastic members may be interposed and arranged between two superposed sheets constituting the sheet laminate, or at least one of the plurality of sheets constituting the sheet laminate may be a stretchable sheet having stretchability. Features provided in only one of the foregoing embodiments may all be used interchangeably among embodiments as appropriate.

In relation to the foregoing embodiments of the present invention (second invention), the following additional remarks (methods for manufacturing fusion-bonded sheet articles; devices for manufacturing fusion-bonded sheet articles) are disclosed.

<1A>

A method for manufacturing a fusion-bonded sheet article that includes sealed edge sections made by fusion-bonding edge sections of a plurality of sheets in a state where the sheets' edge sections are superposed, wherein:

at least one sheet of the plurality of sheets includes a resin material;

the manufacturing method comprises a step of forming the sealed edge sections by making one surface of a belt-shaped sheet laminate in which the plurality of sheets are laminated abut against a support member that has a light passage section through which a laser beam can pass, and irradiating, from the support member side via the light passage section, the belt-shaped sheet laminate, which is in a pressurized state, with a laser beam having a wavelength that is absorbed by the sheets constituting the sheet laminate and that causes the sheets to generate heat, and thus cutting and separating the belt-shaped sheet laminate and, simultaneously, fusion-bonding cut edge sections created, by the cutting/separation, in the plurality of sheets which are in the pressurized state;

a plurality of the fusion-bonded sheet articles are manufactured continuously; and the step of forming the sealed edge sections includes an anterior holding step of arranging the sheet laminate on the outer surface of the support member that travels in a predetermined direction, and holding the sheet laminate in a pressurized state on the outer surface of the support member, an irradiation step of irradiating the sheet laminate, which is held in the pressurized state on the outer surface of the support member, with the laser beam from an inner surface side of the support member via the light passage section, and thus cutting and separating the sheet laminate, and a posterior holding step of, after termination of the laser beam irradiation, holding the cut/separated sheet laminate on the outer surface of the support member while maintaining the pressurized state.

<2A>

The fusion-bonded sheet article manufacturing method as set forth in clause <1A>, wherein the length PL, along the travel direction of the support member, of a region in the support member where the irradiation step is executed is shorter than the length, along the travel direction, of a single piece of the fusion-bonded sheet article.

<3A>

The fusion-bonded sheet article manufacturing method as set forth in clause <1A> or <2A>, wherein the length PL, along the travel direction of the support member, of a region in the support member where the irradiation step is executed is: preferably 0.008 times or greater, more preferably 0.04 times or greater, the length, along the travel direction, of a single piece of the fusion-bonded sheet article; and preferably 0.9 times or less, more preferably 0.8 times or less, the length, along the travel direction, of a single piece of the fusion-bonded sheet article; and more specifically, preferably from 0.008 times to 0.9 times inclusive, more preferably from 0.04 times to 0.8 times inclusive, the length, along the travel direction, of a single piece of the fusion-bonded sheet article.

<4A>

The fusion-bonded sheet article manufacturing method as set forth in any one of clauses <1A> to <3A>, wherein the length PC, along the travel direction of the support member, of a region in the support member where the posterior holding step is executed is from 0.4 times to 12 times, inclusive, the length PL.

<5A>

The fusion-bonded sheet article manufacturing method as set forth in any one of clauses <1A> to <4A>, wherein the length PC, along the travel direction of the support member, of a region in the support member where the posterior holding step is executed is: preferably 0.4 times or greater, more preferably 1 time or greater, even more preferably 1.5 times or greater, the length PL; and preferably 12 times or less, more preferably 7,5 times or less, even more preferably 6 times or less, the length PL; and more specifically, preferably from 0.4 times to 12 times inclusive, more preferably from 1 time to 7.5 times inclusive, even more preferably from 1.5 times to 6 times inclusive, the length PL.

<6A>

The fusion-bonded sheet article manufacturing method as set forth in any one of clauses <1A> to <5A>, wherein: the support member is an annular support member that rotates about a rotation axis; and the sheet laminate is wrapped around an outer peripheral surface of the annular support member.

<7A>

The fusion-bonded sheet article manufacturing method as set forth in clause <6A>, wherein the angle by which the sheet laminate is wrapped around the support member is from 90 degrees to 270 degrees inclusive, and preferably from 120 degrees to 270 degrees inclusive.

<8A>

The fusion-bonded sheet article manufacturing method as set forth in any one of clauses <1A> to <7A>, wherein the length PH, along the travel direction of the support member, of a region in the support member where the anterior holding step is executed is longer than the length, along the travel direction, of a single piece of the fusion-bonded sheet article.

<9A>

The fusion-bonded sheet article manufacturing method as set forth in any one of clauses <1A> to <8A>, wherein:

a plurality of recesses each capable of accommodating a portion of the sheet laminate are formed in the outer surface of the support member at predetermined intervals in the travel direction of the support member; and the length PH, along the travel direction of the support member, of a region in the support member where the anterior holding step is executed is longer than the length, along the travel direction, between two adjacent recesses in the support member.

<10A>

The fusion-bonded sheet article manufacturing method as set forth in any one of clauses <1A> to <9A>, wherein: the thickness of the belt-shaped sheet laminate is partially different; and, in the irradiation step, a section in the sheet laminate having a relatively small thickness is irradiated with the laser beam.

<11A>

The fusion-bonded sheet article manufacturing method as set forth in any one of clauses <1A> to <10A>, wherein the pressurized state of the sheet laminate in each of the anterior holding step, the irradiation step, and the posterior holding step is achieved by: using a pressurizing means including an endless pressurizing belt and a plurality of rollers that rotate in a state where the pressurizing belt is looped thereover; and pressing the pressurizing belt onto a surface of the sheet laminate on the opposite side from the surface abutting against the support member.

<12A>

The fusion-bonded sheet article manufacturing method as set forth in clause <11A>, wherein, if a case where the pressurizing belt is pressed in contact with the annular support member over the entire perimeter in its circumferential direction is considered as 360 degrees, the angular range for wrapping the pressurizing belt around the annular support member is preferably from 90 degrees to 270 degrees inclusive, and more preferably from 120 degrees to 270 degrees inclusive.

<13A>

The fusion-bonded sheet article manufacturing method as set forth in any one of clauses <1A> to <10A>, wherein the pressurized state of the sheet laminate in each of the anterior holding step, the irradiation step, and the posterior holding step is achieved by: using a pressurizing means including a pressing member provided so as to be capable of performing a reciprocating motion between the outer surface of the support member and a predetermined standby position outside the outer surface of the support member, and a cam mechanism that transmits the traveling, in the predetermined direction, of the support member by converting the traveling thereof into reciprocating motion of the pressing member; and pressing the pressing member onto a surface of the sheet laminate on the opposite side from the surface abutting against the support member.

<14A>

The fusion-bonded sheet article manufacturing method as set forth in any one of clauses <1A> to <13A>, wherein, in the posterior holding step, the cut/separated sheet laminate is forcibly cooled.

<15A>

The fusion-bonded sheet article manufacturing method as set forth in any one of clauses <1A> to <14A>, wherein the pressurizing force against the sheet laminate in each step (the anterior holding step, the irradiation step, and the posterior holding step) is: preferably 50 kPa or greater, more preferably 100 kPa or greater; and preferably 160 kPa or less, more preferably 140 kPa or less; and more specifically, preferably from 50 kPa to 160 kPa inclusive, more preferably from 100 kPa to 140 kPa inclusive.

<16A>

The fusion-bonded sheet article manufacturing method as set forth in any one of clauses <1A> to <15A>, wherein all of the sheets constituting a section-to-be-cut/separated in the sheet laminate are sheets that generate heat by absorbing the laser beam.

<17A>

A fusion-bonded sheet article manufacturing device that continuously manufactures a plurality of fusion-bonded sheet articles each having sealed edge sections, by irradiating, with a laser beam, a belt-shaped sheet laminate in which a plurality of sheets are laminated and cutting and separating the sheet laminate, and fusion-bonding cut edge sections created, by the cutting/separation, in the plurality of sheets, the manufacturing device including:

a support member that travels in a predetermined direction in a state where the sheet laminate is arranged on an outer surface of the support member, and that has a light passage section through which a laser beam can pass; an irradiation head that is arranged on an inner surface side of the support member and that emits the laser beam toward the support member; and a pressurizing means that pressurizes, from a side opposite from the support member, the sheet laminate which is arranged on the outer surface of the support member, wherein the support member includes an anterior holding region employed for holding the sheet laminate before being irradiated with the laser beam, a holding region employed for holding the sheet laminate during the laser beam irradiation, and a posterior holding region employed for holding the sheet laminate after being irradiated with the laser beam.

<18A>

The fusion-bonded sheet article manufacturing device as set forth in clause <17A>, wherein the length PL, along the travel direction of the support member, of the holding region of the support member is shorter than the length, along the travel direction, of a single piece of the fusion-bonded sheet article.

<19A>

The fusion-bonded sheet article manufacturing device as set forth in clause <17A> or <18A>, wherein the length PC, along the travel direction of the support member, of the posterior holding region of the support member is from 0.4 times to 12 times, inclusive, the length PL.

<20A>

The fusion-bonded sheet article manufacturing device as set forth in any one of clauses <17A> to <19A>, including, as the pressurizing means, a belt-type pressurizing means including: an endless pressurizing belt; and a plurality of rollers that rotate in a state where the pressurizing belt is looped over the rollers.

<21A>

The fusion-bonded sheet article manufacturing device as set forth in any one of clauses <17A> to <19A>, including, as the pressurizing means, a pressurizing means including: a pressing member provided so as to be capable of performing a reciprocating motion between the outer surface of the support member and a predetermined standby position outside the outer surface of the support member (i.e., outside the annular support member in its radial direction); and a cam mechanism that transmits the rotation of the support member about its central shaft (rotation axis) (i.e., the traveling, in the predetermined direction, of the support member) by converting the rotation (traveling) thereof into reciprocating motion of the pressing member.

The invention claimed is:

1. A method for manufacturing an absorbent article comprising a fusion-bonded sheet article and an absorbent assembly, the method comprising the steps of:

providing a belt-shaped sheet laminate comprising a plurality of sheets, at least one sheet of the plurality of sheets including a resin material;

pressing one surface of the belt-shaped sheet laminate against a support member that has a light passage section through which a laser beam can pass;

irradiating, from a support member side via the light passage section, the belt-shaped sheet laminate which is in a pressurized state with the laser beam having a wavelength that is absorbed by the sheets constituting the sheet laminate and that causes the sheets to generate heat; and cutting and separating the belt-shaped sheet laminate and, simultaneously, fusion-bonding cut edge sections created, by a cutting/separation, in the plurality of sheets which are in the pressurized state to form sealed edge sections, so that the fusion-bonded sheet article is obtained.

2. The absorbent article manufacturing method according to claim 1, wherein the absorbent article is a pull-on disposable diaper, an outer cover that is arranged on a skin-non-contacting surface side of the absorbent assembly and to which the absorbent assembly is fixed, wherein a pair of side seal sections are formed by joining both side edge sections of the outer cover in a stomach-side section and both side edge sections of the outer cover in a back-side section, and the fusion-bonded sheet article is made by folding a belt-shaped outer cover in its width direction, and irradiating a predetermined section of the folded outer cover with the laser beam, and thus, cutting and separating the belt-shaped outer cover and, simultaneously, forming a side seal section.

3. The absorbent article manufacturing method according to claim 1, wherein the absorbent article is an article in which a topsheet forming a skin-contacting surface of the absorbent article and a backsheet forming a skin-non-contacting surface of the absorbent article are joined together in sections extending outward from a peripheral edge of an absorbent core.

4. The absorbent article manufacturing method according to claim 1, wherein the absorbent article is a sanitary napkin, and is made by fusion-bonding: a topsheet and a wing-section forming sheet of the sanitary napkin; or the wing-section forming sheet and a backsheet; or the topsheet, the wing-section forming sheet, and the backsheet.

\* \* \* \* \*